United States Patent [19]

Primakoff et al.

[11] Patent Number: 5,721,348
[45] Date of Patent: Feb. 24, 1998

[54] DNA ENCODING PH-20 PROTEINS

[75] Inventors: Paul Primakoff; Diana G. Myles, both of West Simsbury, Conn.

[73] Assignee: University of Connecticut, Storrs, Conn.

[21] Appl. No.: 779,890

[22] Filed: Oct. 21, 1991

Related U.S. Application Data

[63] Continuation-in-part of Ser. No. 627,782, Dec. 14, 1990, abandoned.

[51] Int. Cl.$^6$ .......................... C07H 19/00; C07H 21/00; C07H 21/04; A61K 35/52
[52] U.S. Cl. .......................... 536/22.1; 536/23.5; 530/350; 530/300; 424/561; 424/559; 424/811
[58] Field of Search ........................... 424/88.92, 184.1, 424/811, 561, 559; 536/27, 22.1, 23.5; 530/350

[56] References Cited

FOREIGN PATENT DOCUMENTS

WO 90/09802  9/1990  WIPO .......................... A61K 39/00

OTHER PUBLICATIONS

Primakoff & Myles, Gamete Interaction: Prospects for Immunocontraception pp. 89–102, Wiley–Liss, Inc. (1990).
Phelps et al. J. Cell Biol., 111: 1839–1847 (1990).
Lathrop et al. J. Cell Biol., 111:2939–2949 (1990).
Phelps et al., Science, 240: 1780–1782 (1988).
Primakoff et al., Nature, 335: 543–546 (1988).
Primakoff et al., Biol. Reprodu., 38:921–934 (1988).
Phelps & Myles, Dev. Biol., 123: 63–72 (1987).
Myles et al., Dev. Biol., 121: 559–567 (1987).
Cowan et al., J. Cell Biol., 103: 1289–1297 (1986).
Primakoff et al., J. Cell Biol., 101: 2239–2244 (1985).
Primakoff et al., J. Cell. Biol. 104: 141–149 (1987).
Blobel et al., *J. Cell Biol.* 111: 69–78 (1990).
Site–Specific Endeproterlytic Activity in Sperm Preporalus that Cleunes PH 20 into Two Disulfide–Linked Fragments. Lathrop et al. J. Cell Biol. 109:125a Abst # 674 Nov. 5–9 1989. Cloning & Sequency of the Gene for the PH 20 protein of Guinea Sperm.
Young et al (PNAS 80:1194–1198, 1983) Efficient isolation of genes by using antibody probes.
Lathrop et al J. Cell Biol. 111:2939–2949, 1990 cDNA Cloning Reveals the Molecular Structure of a Sperm Surface Protein PH 20, Involved in Sperm–Egg Adhesion & the Wide Distribution of its Gene Among Mammals.
Primakoff et al. Biology of Reproduction 38:921–934 1988 Purification of the Guinea Pig Sperm PH 20 Antigen & Detection of a Sambrook Molecular Cloning Chapter 17 Expression of Cloned Genes in *Escherichia coli*.
Int'l Search Report 18 Sep. 1991 PCT Int'l.
Lin et al PNAS, Molecular Cloning of the Human & Monkey sperm surface protein PH 20 90: 10011–10015 1993.
Aitken et al, British Medical Bulletin 49: 88–99, 1993 Contraceptive Vaccine.
Naz et al Human Reproduction 5:511–518, 1990. Review Development of antisperm contraceptive vaccine for humans: Why & How?.

*Primary Examiner*—Hazel F. Sidberry
*Attorney, Agent, or Firm*—Hamilton, Brook, Smith & Reynolds, P.C.

[57] ABSTRACT

The disclosure relates to isolated DNA encoding all or a portion of a surface protein present in sperm of a mammal. This surface protein of sperm is essential for fertilization in the mammal. Preferably, the sperm surface protein is the PH-20 protein.

6 Claims, 1 Drawing Sheet

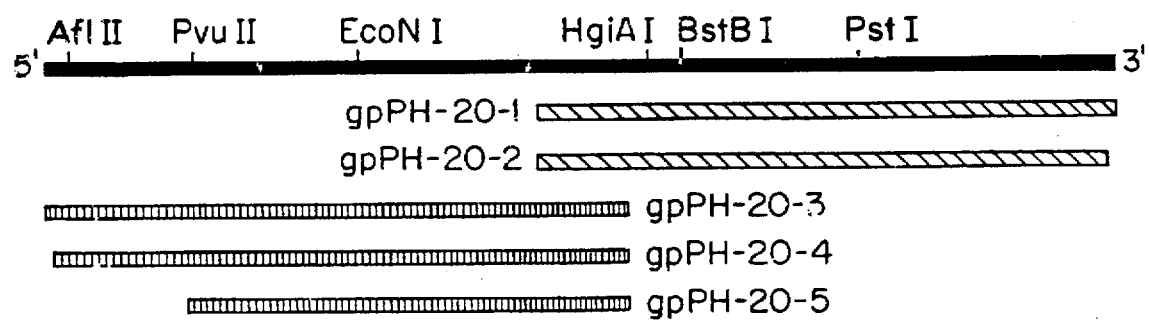

DNA ENCODING PH-20 PROTEINS

RELATED APPLICATIONS

This application is a continuation-in-part of Ser. No. 07/627,782, filed Dec. 14, 1990, now abandoned, the contents of which are hereby incorporated by reference.

GOVERNMENT SUPPORT

Research described in this application was funded by National Institute of Health Grants HD-21989 and HD-16580.

BACKGROUND

Immunization of male and female animals with extracts of whole sperm cells is known to cause infertility (Tung, K., et al., *J. of Reproductive Immunol.*, 1: 145–158 (1979) and Menge, A., et al., *Biol. of Reproduction*, 20: 931–937 (1979)). Also, men and women who spontaneously produce antisperm antibodies are infertile, but otherwise healthy (Bronson, R. et al., *Fert. and Steril.*, 42: 171–183 (1984)). Although the critical sperm antigens are unknown, these observations have led to the proposal that sperm proteins might be useful in the development of a contraceptive vaccine.

In mammalian species, sperm proteins have been proposed to have a role in sperm adhesion to the zona pellucida of the egg. In the mouse, it has been shown that a sperm surface galactosyl transferase is an adhesion protein that functions in acrosome-intact sperm binding to the zona (Shut, B. E., *Galactosyl transferase as a recognition molecule during fertilization and development*, In: "The Molecular Biology of Fertilization," Eds. Schatten, H., and Schatten, G., Academic Press, pps. 37–71 (1989)). On rat sperm, there is a galactose receptor, (RTG-r), related to the hepatic asialoglycoprotein receptor, which could function through its lectin properties in sperm binding to zona oligosaccharides (Abdullah, M., and Kierszenbaum, A. L., *J. Cell Biol.*, 108: 367–375 (1989)). A boar sperm plasma membrane protein ($AP_z$), distinct from galactosyl transferase, and a rabbit sperm protein have also been reported to have a role in sperm-zona adhesion (Peterson, R. N. and Hunt, W. P., *Gam. Res.*, 23: 103–118 (1989) and O'Rand, M. G., et al., *Dev. Biol.*, 129: 231–240 (1988)).

The guinea pig sperm surface protein PH-20 has been shown to have a required function in sperm adhesion to the extracellular coat (zona pellucida) of the egg, a necessary initial step in fertilization. In male and female guinea pigs immunized with PH-20, 100% effective contraception was obtained. Antisera from immunized females had high titers, specifically recognized PH-20 sperm extracts and blocked adhesion to egg zona pellucida, in vitro. The contraceptive effect was long-lasting and reversible; immunized females mated at intervals of 6–15 months after immunization progressively regained fertility.

Other sperm proteins tested as contraceptive immunogens include the sperm enzymes hyaluronidase, acrosin and lactate dehydrogenase C-4. Immunization of female animals with these enzymes had either no effect on fertility or partial effects on fertility, which were not large enough to make these proteins suitable as contraceptive agents. The high contraceptive effectiveness of PH-20, in the guinea pig, seems to depend on several of its specific properties, including its presence on the sperm surface, its strong immunogenicity and its essential role in fertilization.

Mammalian sperm-zona adhesion is in most cases species specific. Sperm from other mammalian species are like guinea pig sperm in that they can bind to the zona pellucida either before or after the acrosome reaction. The identification and isolation of sperm surface proteins essential for fertilization in species other than guinea pig would be useful for developing vaccines for effective immunization and providing long lasting contraception in those species. The lack of biochemical identification, isolation and cloning of candidate adhesion proteins of sperm has hindered scientists in developing effective contraceptive vaccines for humans as well as other mammalian species.

SUMMARY OF THE INVENTION

The present invention relates to isolated DNA encoding all or a portion of a surface protein present in the sperm of a mammal. This surface protein of sperm is essential for fertilization in the mammal. Preferably the surface protein is the protein PH-20. Such DNA sequences can be inserted, in expressible form, into a DNA expression vector to create a DNA expression construct. Such a construct can be used to produce PH-20 protein for use in contraceptive immunization.

Current methods of contraception include physical and chemical methods such as surgical sterilization and drug treatments which alter the production of female hormones and interrupt the reproductive cycle. Each of these types of methods present their own distinct disadvantages. Sterilization, requiring surgery, causes permanent contraception and cannot, in general, be changed once performed. Barrier methods have lower theoretical effectiveness, low effectiveness in practice and are unacceptable to many potential users. The chemical methods provide temporary contraception and have been reported to cause an increased risk in cancer for women in certain age brackets. They must be taken repeatedly to ensure effectiveness and have actual or perceived side effects that make them unacceptable to many women. Chemical methods are not available for men and are not available for other mammals.

The present invention provides an alternative approach to contraception as a contraceptive vaccine that is longer lasting than the oral contraceptive pill yet is not a permanent form of contraception such as occurs with surgical sterilization. Hence, the present invention is as effective or more effective than other methods of contraception, is more convenient and utilizes the widely accepted medical practice of vaccination. In addition, it is more suitable than various other alternatives in that it is long lasting but not permanent.

BRIEF DESCRIPTION OF THE DRAWINGS

The FIG. 1 is a diagram representing a partial restriction map of DNA encoding the guinea pig PH-20 protein, and the relative positions of 5 cDNA clones.

SEQ ID NO: 1 is a diagram representing the guinea pig cDNA sequence encoding the PH-20 protein, and the deduced amino acid sequence of the guinea pig PH-20 protein presented in three letter code.

SEQ ID NO: 3 is a diagram representing the murine DNA sequence encoding the PH-20 protein.

SEQ ID NO: 5 is a diagram representing the human DNA sequence encoding one form of the human PH-20 protein, and the deduced amino acid sequence presented in three letter code is represented in SEQ ID NO: 6.

SEQ ID NO: 7 is a diagram representing the human DNA sequence encoding a portion of a second form of the human PH-20 protein, and the deduced amino acid sequence presented in three letter code is represented in SEQ ID NO: 8.

DETAILED DESCRIPTION OF THE INVENTION

The PH-20 gene encodes a protein which is present on the surface of sperm cells and is essential for fertilization. The present invention is based, in part, on the isolation and cloning of DNA encoding the mammalian PH-20 protein and the discovery that the DNA encoding PH-20 in one mammalian species is cross-reactive (i.e., hybridizable) with genomic DNA from all other mammals tested. The existence of these homologues in other mammalian species was an unexpected finding since mammalian sperm-zona pellucida adhesion is, in most cases, species specific.

Sperm Surface Proteins

Sperm surface proteins which are useful in the present invention include surface proteins which are essential for fertilization. A sperm surface protein is defined as essential for fertilization if a monoclonal antibody to the protein or a polyclonal antibody raised against the purified protein, when bound to sperm, inhibits in vitro or in vivo fertilization or any step in in vitro fertilization. The process of fertilization is defined as the binding or fusion of two gametes (sperm and egg) followed by the fusion of their nuclei to form the genome of a new organism. The surface protein can be located in the plasma membrane of sperm and/or the inner acrosomal membrane. It can be a protein or glycoprotein. The isolated surface protein used for immunization can comprise the entire surface protein or some portion of the protein (external to the cell) which is immunogenic. A preferred sperm surface protein is the PH-20 surface protein.

Production and Purification of Immunogen

A preferred method for producing sperm surface proteins for use as a contraceptive immunogen is by recombinant DNA technology. To produce the protein using this technology it is necessary to isolate and clone DNA encoding the protein, or an immunogenic portion thereof. Those skilled in the art are familiar with a variety of approaches which can be used in an effort to clone a gene of interest. However, having nothing more than the isolated protein of interest, success in such an effort can not be predicted with a reasonable degree of certainty.

In Example 1 which follows, Applicants' report the isolation and cloning of DNA encoding the guinea pig PH-20 gene. The method used to isolate DNA encoding the 3' portion of the PH-20 gene involved the screening of a cDNA expression library with polyclonal sera reactive with the PH-20 protein. Anchored PCR was used to isolate the 5' portion of the gene.

Example 2 reports the surprising finding that a broad spectrum of mammalian genomic DNA contains DNA sequences which hybridize to guinea pig PH-20 sequences under the hybridization conditions described. In fact, cross-reacting sequences were identified in each of the mammalian samples analyzed.

The information presented in Examples 1 and 2, enable one skilled in the art to isolate and clone the PH-20 gene from any mammalian species. For example, a cDNA library is prepared from testis or spermatogenic cells isolated from a mammal of interest (e.g., feline, equine, canine, bovine, etc.). This can be a time consuming process, but it is technically straightforward. One skilled in the art would approach this task with a high degree of certainty with regard to success.

Such a cDNA library is then screened using, for example, labeled guinea pig PH-20 DNA probes. DNA encoding all or a portion of PH-20 is characterized by the ability to hybridize to such a probe sequence under hybridization conditions such as those described in Example 2. Methods of labeling and screening by hybridization are very well known in the art. Positive clones are analyzed, and a full length gene is constructed by conventional methods. In light of Applicants' teaching that each of the 7 mammals analyzed contained cross-hybridizing sequences, one skilled in the art would expect all mammals to contain cross-hybridizing species. It is this methodology which enabled Applicants to isolate and clone the murine and human PH-20 genes, as described in greater detail below.

The cloned gene, or portions thereof which encode an immunogenic region of the PH-20 protein, can be expressed by inserting the coding region into an expression vector to produce an expression construct. Many such expression vectors are known to those skilled in the art. These vectors contain a promoter for the gene of interest as well as additional transcriptional and translational signals. Expression vectors for both eukaryotic host cells and prokaryotic host cells are widely available. The DNA expression construct is used to transform an appropriate host cell.

Eukaryotic, in particular mammalian, host cells are preferred for the expression of the sperm surface protein. It has been found, for example, that eukaryotic proteins frequently exhibit folding problems when expressed in prokaryotic cells. In addition, production of authentic, biologically active eukaryotic proteins from cloned DNA frequently requires post-translational modification such as disulfide bond formation, glycosylation, phosphorylation or specific proteolytic cleavage processes that are not performed in bacterial cells. This is especially true with membrane proteins. The sperm surface protein is produced using the transcriptional and translational components of the host cell. After an appropriate growth and expression period, the host cell culture is lysed and the sperm surface protein is purified from the lysate. Lysis buffers typically include non-ionic detergent, chelating agents, protease inhibitors, etc.

From the solubilized cell extract, the sperm surface protein can be purified and isolated by physical and biochemical methods such as ultracentrifugation, column chromatography, high performance liquid chromatography, electrophoresis, etc. Alternatively, the sperm surface protein can be isolated by affinity chromatography using monoclonal or polyclonal antibodies (see Primakoff et al., *Biol. of Reprod.* 38: 921–934 (1988)). Such methods for purifying proteins are well known to those skilled in the art.

As mentioned above, antigenic portions of the sperm surface protein are useful as immunogen, in addition to the full length protein. Antigenic fragments can be produced, for example, by proteolytic digestion of the full length protein, followed by isolation of the desired fragment. Alternatively, chemical synthesis can be used to generate the desired fragment starting with monomer amino acid residues.

Contraceptive Vaccine

Once the sperm surface protein has been produced and purified, a vaccine can be produced by combining the sperm surface protein with a suitable carrier for administration to a subject for immunization. A vaccine can contain one or more sperm surface proteins. Sperm surface proteins of the present invention can be combined with adjuvants which contain non-specific stimulators of the immune system. Proper use of adjuvants can induce a strong antibody response to foreign antigens (i.e., sperm surface proteins). The action of adjuvants is not fully understood, but most adjuvants incorporate two components. One is a substance designed to form a deposit which protects the antigen from catabolism. Two methods of forming a deposit are to use mineral oils or aluminum hydroxide precipitates. With mineral oils, such as Freund's adjuvant, the immunogen is prepared in a water-in-oil emulsion. For aluminum hydroxide, the immunogen is either adsorbed to preformed precipitants or is trapped during precipitation. Alternative delivery systems include liposomes or synthetic surfactants. Liposomes are only effective when the immunogen is incorporated into the outer lipid layer; entrapped molecules are not seen by the immune system.

The second component required for an effective adjuvant is a substance that will stimulate the immune system non-specifically. These substances stimulate the production of a large set of soluble peptide factors known as lymphokines. In turn, lymphokines stimulate the activity of antigen-processing cells directly and cause a local inflammatory reaction at the site of injection. A component of lipopolysaccharide known as lipid A is commonly used. Lipid A is available in a number of synthetic and natural forms that are much less toxic than lipopolysaccharides, but still retain most of the desirable adjuvant properties of the lipopolysaccharide molecules. Lipid A compounds are often delivered using liposomes. The two bacteria that are commonly used in adjuvants as non-specific stimulants are *Bordatella pertussis* and *Mycobacterium tuberculosis*. When used as whole bacteria, they must be heat-killed prior to use. The immunomodulatory mediators of *B. pertussis* include a lipopolysaccharide component and the pertussis toxin. The pertussis toxin has been purified and is available commercially. *M. tuberculosis* is commonly found in complete Freund's adjuvant. The most active component of *M. tuberculosis* has been localized to muramyl dipeptide which is available in a number of forms.

Immunizations (Inoculation and Booster Shots)

The subject to be immunized can be any mammal which possesses a competent immune system. Examples of subject mammals include humans and domestic animals (e.g., dogs, cats, cows, horses, etc.), as well as animals intended for experimental or other purposes (e.g., mice, rats, rabbits, etc.).

Two different criteria are important to consider in determining the proper dose for the initial immunization. First, the optimum dose to achieve the strongest response and second, the minimum dose likely to induce the production of useful polyclonal antibodies. Much of the injected material will be catabolized and cleared before reaching the appropriate target immune cell. The efficiency of this process will vary with host factors, the route of injection, the use of adjuvants, and the intrinsic nature of the surface protein injected. Thus, the effective dose delivered to the immune system may bear little relationship to the introduced dose and consequently dose requirements must be determined empirically. These determinations can be readily made by one skilled in the art. Secondary injections and later boost can be given with amounts similar to or less than the primary injection.

The route of injection is guided by three practical decisions: 1) what volume must be delivered; 2) what buffers and other components will be injected with the immunogen; and 3) how quickly the immunogen should be released into the lymphatics or circulation. For example, with rabbits, large volume injections normally are given at multiple subcutaneous sites. For mice, large volumes are only possible with intraperitoneal injections. If adjuvants or particulate matter are included in the injection, the immunogen should not be delivered intravenously. If a slow release of the inoculant is desired, the injections should be done either intramuscularly or intradermally. For immediate release, use intravenous injections.

Primary antibody responses often are very weak, particularly for readily catabolized, soluble antigens. Hence, secondary or booster injections are required after the initial immunization. A delay is needed before reintroducing the protein into a primed subject. A minimum of 2 or 3 weeks is recommended but greater intervals are possible. The antibody responses to secondary and subsequent injections is much stronger. Higher titers of antibody are reached, but more importantly, the nature and quantity of the antibodies present in serum changes. These changes yield high-affinity antibodies. The intervals between secondary, tertiary and subsequent injections may also be varied, but usually need to be extended to allow the circulating level of antibody to drop enough to prevent rapid clearance of newly injected antigen.

Subsequent booster injections will be required to increase reduced circulating antibody for continued contraception. The actual intervals for these injections will differ form species to species. However, the intervals can be determined by one skilled in the art by monitoring serum levels of sperm surface protein antibodies.

In another embodiment, subjects can be administered with alloantisera, or monoclonal antibodies, directed to a sperm surface protein to achieve contraception. The alloantiserum is raised in another individual of the same species, isolated from the serum of the individual and prepared in a suitable carrier for injection into the recipient subject. Those skilled in the art are familiar with methods for preparing and formulating monoclonal antibodies for administration.

The present invention is further explained in the following exemplification.

EXAMPLES

Example 1

Isolation of DNA Encoding Guinea Pig PH-20

Library construction and screening

A population of guinea pig testicular cells, enriched for spermatogenic cells on a Percoll gradient was used for the isolation of spermatogenic cell total RNA. The pelleted cells were lysed with detergent in the presence of vanadyl-ribonucleoside complexes (VRC) in 0.5–1.0 ml of solution containing 10 mM Tris (pH 8.6), 0.5% NP-40, 0.14M NaCl, 1.5 mM $MgCl_2$ and 10 mM VRC. After pelleting cellular debris, 0.5 volume of 2X Proteinase K buffer (2X=0.2M Tris (pH 7.5), 25 mM EDTA (pH 8.0), 0.3M NaCl, and 2.0% SDS) and 200 µg/ml Proteinase K was added to the supernant. PolyA+ RNA was purified from the total RNA by oligo-dT cellulose chromatography. cDNA was synthesized using standard methods. Size selected cDNA (0.5–7kb) was ligated with lambda gt11 arms and packaged into lambda coat proteins, utilizing kits and protocols from Amersham Corporation.

The unamplified library was plated at 20,000 plagues/150 mm plate for screening. A single nitrocellulose filter from each plate was immunoblotted with rabbit anti-PH-20 polyclonal antiserum, raised against affinity-purified PH-20 protein (Primakoff et al., *Biol. Reprod.* 38: 921–934 (1988)), and diluted 1/500 in TBST (10 mM Tris (pH 8.0), 0.15M NaCl, 0.05% Tween-20) containing 2 mg/ml *E. coli* protein. The *E. coli* protein was prepared by pelleting an overnight culture of Y1090 cells, resuspending the cells in a minimal volume of TBST and freezing in liquid nitrogen. The thawed cells were sonicated and the protein concentration determined using the BCA reagent (Pierce Chemical). Six positive plaques were detected with an anti-rabbit IgG alkaline phosphatase-conjugated second antibody (Promega Biotec). Sizes of the fusion protein made by plaque-purified positive clones were determined to vary between 118–157 kD as determined by the analysis of *E. coli* extracts containing the fusion protein on SDS-PAGE. Inserts from the six positive clones were subcloned into pUC19 and sequenced at least partially.

Two of the inserts were confirmed to code for the PH-20 protein by locating the sequences of two PH-20 tryptic peptides in their derived amino acid sequence. Both of these inserts (gpPH-20-1, nucleotide (nt) 1016–2152 and gpPH-20-2, nt 1010–2125, the FIGURE and SEQ ID NO: 1) contained a long (~925 nt) open reading frame, a stop codon, a 3' untranslated region and a polyA tail. Thus these two inserts were concluded to represent the 3' end of a cDNA for PH-20. The other four antibody-positive lambda clones were unrelated to PH-20.

The 5' portion of the PH-20 cDNA was cloned utilizing anchored PCR following the protocol of Frohman et al. (*Proc. Natl. Acad. Sci. USA* 85: 8998–9002 (1988)). PolyA+ RNA from spermatogenic cells (2 µg in 10 µl dH$_2$O) was heated to 65° C. for 3 min and then reverse transcribed by adding 4 µl 10 X RTC buffer (1X buffer is 50 mM Tris (pH 8.3), 50 mM KCl, 4 mM dithiothreitol, 10 mM MgCl$_2$)), and 4 µl 1 10 mM stock of each dNTP (1 mM final), 2 µl of 80 mM sodium pyrophosphate (4 mM final), 1 µl (40 units) of RNasin (Promega Biotec), 40 pmol PH-20 specific primer (PH-20-RT), 18 units AMV reverse transcriptase (Life Sciences) and 40 µCi 32P-dCTP in 40 µl total volume. After 1 hour of incubation at 42° C., an additional 1 µl of reverse transcriptase was added and incubation continued for a second hour. The PH-20-RT primer was a 17 nucleotide (nt) oligomer (nt 1242–1258, SEQ ID NO: 1), ~250 bases downstream from the 5' end of the insert gpPH-20-1 (the FIGURE).

The single strand cDNA was separated from excess PH-20-RT by column chromatography, tailed with polyA and diluted to 1.0 ml. Second strand synthesis and PCR amplification were performed with a GeneAmp kit (Perkin Elmer Cetus) in a 100 µl reaction containing 10 µl of the reverse transcription product, 20 pmol (dT) 17 adapter, 50 pmol adapter and 50 pmol PH-20-AMP primer. The PH-20-AMP primer was a 17 nt oligomer (nt 1202–1218, SEQ ID NO: 1) located upstream from the PH-20-RT primer. The PCR product was purified from unincorporated primers and free nucleotides by spin column chromatography (columns from Boehringer-Mannheim). It was subsequently digested with HgiA I and Sal I, gel purified and ligated into pBluescript digested with Pst I and Sal I. The major PCR product was 1.2 kb, and Southern Blot analysis confirmed that this band hybridized with the labeled insert gpPH-20-1. The major PCR products from three separate reactions were cloned and one insert from each of the three reactions was sequenced (gpPH-20-3, nt 1–1175, gpPH-20-4, nt 24–1175 and gpPH-20-5, nt 295–1175).

The complete cDNA sequence and the deduced amino acid sequence were obtained from the five cDNA inserts (SEQ ID NO: 1) that were sequenced in their entirety on both strands. The cDNA sequence contains a 354 nt 5' untranslated region, a 1590 nt open reading frame, and a 208 nt 3' untranslated region. The derived amino acid sequence contains all the tryptic peptide sequences obtained from purified PH-20, confirming that the cDNAs are authentic PH-20 clones. Hybridization experiments indicated that guinea pig genomic DNA contained a single gene for PH-20. Computer searches revealed no significant homology of the guinea pig PH-20 amino acid sequence with other known sequences.

Example 2

PH-20 Homologues in Other Mammalian Species

To determine if there is a homologue of the PH-20 gene in the genomic DNA of other species, cross species Southern blots were performed. Genomic DNA was isolated from guinea pig, rat, rabbit, mouse, and hamster spleens by detergent lysis-Proteinase K digestion. Other DNA samples (i.e., human, monkey and chicken) were provided by other investigators at the University of Connecticut Health Center. DNA from salmon sperm and bovine thymus were purchased from Sigma and reconstituted at 1 mg/ml in TE (10 mM Tris (pH 8.0), 1 mM EDTA (pH 8.0)). All species DNA's (10 µg) were cut with restriction enzymes and separated on a 1% agarose gel. The Southern transfer was carried out by capillary transfer onto nylon membrane. The membranes were prehybridized in a solution consisting of 6XSSC, 1X Denhardt's, 250 mg/ml salmon sperm DNA, 1% SDS, and 50 mM NaPO$_4$ (pH 7.4), for 1–2 hours at 65° C. The membranes were hybridized overnight at 55° C. in prehybridization buffer plus 2×10$^6$ cpm/ml probe. Probes were prepared by the random hexamer method. The blot was washed 3×5 min in 2XSSC+1.0% SDS at room temperature, 2×30 min in 2XSSC+0.1% SDS at 50° C., and 2×30 min in 1XSSC+0.1% SDS at 60° C. The blot was wrapped in plastic wrap and exposed to film with an intensifying screen at −70° C.

The blots were probed with a mix of labeled gpPH-20-3 and gpPH-20-2. The Southern blots exhibited a weakly hybridizing band at ~10 kb for chicken DNA and strongly hybridizing bands for mouse, rat, hamster, rabbit and human DNA. In addition, hybridization was observed with bovine and monkey DNA.

Example 3

Isolation of DNA Encoding Mouse PH-20

PolyA+ RNA was isolated from murine round spermatids and used to produce a cDNA library in lambda J using conventional methods. The library was screened using a labeled full length guinea pig PH-20 cDNA probe. The probe was produced by first isolating guinea pig PolyA+ RNA. An oligo-dT primer was hybridized to the poly(A) tract and reverse transcriptase was used to generate a first cDNA strand. Two oligonucleotides, a first being complementary to a portion of the guinea pig PH-20 5' untranslated region and a second being complementary to the 3' untranslated region, were added to the reaction mixture and a full length double stranded DNA sequence containing the entire coding region was generated by polymerase chain reaction. The product of this reaction was a double stranded DNA fragment of between 1.5–1.6 kb. The fragment was cloned and the cloned fragment was analyzed to confirm that it did, in fact, encode the guinea pig PH-20 protein. Labeled probe was generated from this clone by conventional methods.

The murine cDNA library was screened using the guinea pig probe described above. Two positive clones were identified. The two clones represent about 1500 base pairs of DNA. Neither of the clones contained sequences from the 5' portion of the cDNA. Anchored PCR using a set of primers complementary to the 5' end of one of the positive clones was used to clone the 5' portion of the murine gene. The DNA sequence is set forth in SEQ ID NO: 3.

Example 4

Isolation of DNA Encoding Human PH-20

DNA encoding human PH-20 was isolated and cloned by screening a human testis library in lambda gt11. The library was plated at a density of about 3,000 plaques per 90 mm plate. Phage plaques were transferred to duplicate filters and screened with a mix of two radioactively labeled DNA probes, a mouse PH-20 cDNA and a guinea pig PH-20 cDNA. More specifically, the guinea pig probe was the labeled full length guinea pig PH-20 probe described above and the murine clone was one of the two murine clones which lacked sequences from the 5' end of the murine cDNA.

Positive plaques that hybridized with the mix of two probes were picked and purified. The cDNA inserts were subcloned and the DNA sequence determined using standard techniques. Two cDNA clones were obtained. Each of the two encode a different form of human PH-20. One human clone is designated H18 (SEQ ID NO: 5) and one is designated H16 (SEQ ID NO: 7).

H18 is a full-length clone which contains an open reading frame of 510, amino acids SEQ ID NO: 6 and short 5' and 3' untranslated regions. The protein encoded in the open reading frame of H18 is 59% identical and 74% similar (includes conservative substitutions) to guinea pig PH-20.

H16 is a partial length clone that encodes the carboxyl terminal half of human PH-20 (SEQ ID NO: 8). Nucleotide 1 in H16 corresponds with nucleotide 814 in H18. The sequence of H16 from nucleotide 1–781 is identical to the sequence of H18 from nucleotide 814–1594; the sequence of H16 beginning at nucleotide 782 and continuing to nucleotide 1675 is different from the sequence of H18 beginning at nucleotide 1595 and continuing to nucleotide 1696. In terms of the encoded PH-20 protein, the partial protein encoded by H16 is identical to the protein encoded by H18 between amino acids 236–496 (amino acid numbering based on sequence). H16 then encodes amino acids 497–511 and H18 encodes amino acids 497–510 and the sequences are different at each residue.

Expression and Purification of Human PH-20

The full-length clone for PH-20 (H18) was subcloned into two E- coli expression vectors, pMAL-p and pMAL-c (New England Biolabs, Beverly, Mass.). In both vectors, PH-20 is made as a fusion protein, the N-terminal fusion partner being the maltose binding (MBP) protein of *E. coli*. In pMAL-p, the encoded MBP (which is normally a periplasmic protein) has its usual signal sequence which results in the MBP-PH-20 fusion being targeted to the periplasm. For fusion proteins that can be successfully exported to the periplasm, this location has the advantage that disulfide bonds form (twelve cysteines are present in human PH-20) yielding a potentially more immunogenic protein. In pMAL-c, the signal sequence for MBP is not present, and the fusion protein is found in the cytoplasm and does not form disulfides. Human PH-20 is produced from both pMAL-p and pMAL-c. However, in pMAL-p carrying strains, the amount of hPH-20 made is low, whereas in pMAL-c carrying strains, the amount of PH-20 made is high (the fusion protein is the major band in an *E. coli* extract on a Coomassie blue-stained SDS-PAGE gel). To purify the human PH-20 fusion protein, the MBP-PH-20 fusion protein is bound to an amylose resin (to which MBP binds) and eluted with maltose.

Equivalents

Those skilled in the art will recognize, or be able to ascertain using no more than routine experimentation, many equivalents to the specific embodiment of the invention described specifically herein. Such equivalents are intended to be compassed in the scope of the following claims.

---

We claim:

1. Isolated DNA wherein the isolated DNA encodes a polypeptide selected from the group consisting of:
   (a) a polypeptide comprising an amino acid sequence of SEQ ID NO: 6; and
   (b) a polypeptide comprising an amino acid sequence SEQ ID NO: 8.

2. Isolated DNA of claim 1, wherein the DNA is characterized by the ability to hybridize to a DNA comprising a sequence selected from the group consisting of SEQ ID NO: 5 and SEQ ID NO: 7.

3. A DNA expression construct comprising DNA encoding a polypeptide selected from the group consisting of:
   (a) a polypeptide comprising an amino acid sequence of SEQ ID NO: 6; and
   (b) a polypeptide comprising an amino acid sequence of SEQ ID NO: 8.

4. A DNA expression construct of claim 3, wherein the DNA is characterized by the ability to hybridize to a DNA comprising a sequence selected from the group consisting of SEQ ID NO: 5 and SEQ ID NO: 7.

5. Isolated DNA encoding a human PH-20 protein, wherein the DNA hybridizes to DNA comprising SEQ ID NO:5 or SEQ ID NO:7, under hybridization conditions of prehybridization for 1–2 hours at 65° C. in prohybridization solution consisting of 6X SSC, 1X Denhardt's solution, 250 mg/ml salmon sperm DNA, 1% SDS and 50 mM $NaPO_4$ at pH 7.4, hybridization overnight with probe at 55° C. in prohybridization buffer, and 3 washes of 2X SSC+1.0% SDS for 5 minutes at room temperature, 2 washes of 2X SSC+ 0.1% SDS for 30 minutes at 50° C. and 2 washes of 1X SSC+0.1% SDS for 30 minutes at 60° C.

6. Isolated DNA which encodes a human PH-20 protean, wherein the DNA is characterized by the ability to hybridize to a DNA comprising SEQ ID NO: 1 or SEQ ID NO:3 under hybridization Conditions of prohybridization for 1–2 hours at 65° C. in prohybridization solution consisting of 6X SSC, 1X Denhardt's solution, 250 mg/ml salmon sperm DNA, 1% SDS and 50 mM $NaPO_4$ at pH 7.4, hybridization overnight with probe at 55° C. in prohybridization buffer, and 3 washes of 2X SSC+1.0% SDS for B minutes at room temperature, 2 washes of 2X SSC+0.1% SDS for 30 minutes at 50° C. and 2 washes of 1X SSC+0.1% SDS for 30 minutes at 60° C.

* * * * *

UNITED STATES PATENT AND TRADEMARK OFFICE
CERTIFICATE OF CORRECTION

PATENT NO. : 5,721,348
DATED : February 24, 1998
INVENTOR(S) : Paul Primakoff and Diana G. Myles It is certified that error appears in the above-identified patent and that said Letters Patent is hereby corrected as shown below:

| | |
|---|---|
| In Column 36, line 10: | After the words "65°C, in", delete "prohybridization" and insert therefor --prehybridization--; |
| In Column 36, line 15: | Before the word "buffer," delete the word "prohybridization" and insert therefor --prehybridization--; |
| In Column 36, line 23: | After the word "hybridization", delete "Conditions of prohybridization" and insert therefor --conditions of prehybridization--; |
| In Column 36, line 24: | Before the word "solution", delete "prohybridization" and insert therefor --prehybridization--; |
| In Column 36, line 27: | Before the word "buffer", delete "prohybridization" and insert therefor --prehybridization--; and |

UNITED STATES PATENT AND TRADEMARK OFFICE
CERTIFICATE OF CORRECTION

PATENT NO. : 5,721,348
DATED : February 24, 1998
INVENTOR(S) : Paul Primakoff and Diana G. Myles It is certified that error appears in the above-identified patent and that said Letters Patent is hereby corrected as shown below:

In Column 36, line 28:   After "SDS", delete "for B minutes" and insert therefor --for 5 minutes--.

Signed and Sealed this

Fifth Day of May, 1998

*Attest:*

BRUCE LEHMAN

*Attesting Officer*   Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 2152 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 355..1941

( x i ) SEQUENCE DESCRIPTION: SEQ ID NO:1:

```
GCTTTACTGT  GAGGTTGCTT  GTACATTGAT  TTTCCAGTTC  TCTTAAGAAT  CTGTGGCTTG        60

ATGTAGCTCA  CACGAATCCA  GGAGGATTTT  TGTTTCTTAA  TTTTGATGAC  TGCGTACATG       120

ATTAGTAGTA  CATCGTAAAG  TCTCTTCCAA  CAAGTTACAG  ATGGTGCAAC  ATTCAAAACA       180

TTCCTGAAAT  ACAAAACAAG  AAGAATATTT  TAATGTAACA  GAGTTGTTTA  CCTCTTTATC       240

CACCAAAGTG  ACCTCACTGT  ACTACGCTTC  TTTTGGGCTC  ATATTGTGCA  ACAAATATTG       300

GAAAAAACAG  TGTATAAGAA  GAAAAAGTAT  TTTTCACAGC  TGTTACTCTT  TCTA ATG        357
                                                               Met
                                                                1

GGA  GCA  TTC  ACT  TTT  AAA  CAC  AGC  TTT  TTT  GGG  AGT  TTT  GTT  GAG  TGC      405
Gly  Ala  Phe  Thr  Phe  Lys  His  Ser  Phe  Phe  Gly  Ser  Phe  Val  Glu  Cys
      5              10                      15
```

| | | | | | | | | | | | | | | | | |
|---|---|---|---|---|---|---|---|---|---|---|---|---|---|---|---|---|
| AGT | GGA | GTA | TTG | CAG | ACA | GTG | TTT | ATT | TTC | CTT | CTA | ATT | CCA | TGT | TGC | 453 |
| Ser | Gly | Val | Leu | Gln | Thr | Val | Phe | Ile | Phe | Leu | Leu | Ile | Pro | Cys | Cys | |
| | | 20 | | | | 25 | | | | | 30 | | | | | |
| CTG | GCT | GAT | AAA | AGG | GCA | CCA | CCA | CTC | ATC | CCA | AAT | GTG | CCT | TTG | CTC | 501 |
| Leu | Ala | Asp | Lys | Arg | Ala | Pro | Pro | Leu | Ile | Pro | Asn | Val | Pro | Leu | Leu | |
| | | 35 | | | | 40 | | | | | 45 | | | | | |
| TGG | GTC | TGG | AAT | GCC | CCA | ACT | GAA | TTT | TGT | ATA | GGA | GGA | ACC | AAT | CAA | 549 |
| Trp | Val | Trp | Asn | Ala | Pro | Thr | Glu | Phe | Cys | Ile | Gly | Gly | Thr | Asn | Gln | |
| 50 | | | | | 55 | | | | | 60 | | | | | 65 | |
| CCA | CTA | GAT | ATG | AGC | TTT | TTC | TCT | ATA | GTA | GGA | ACT | CCC | AGG | AAA | AAT | 597 |
| Pro | Leu | Asp | Met | Ser | Phe | Phe | Ser | Ile | Val | Gly | Thr | Pro | Arg | Lys | Asn | |
| | | | | 70 | | | | | 75 | | | | | 80 | | |
| ATC | ACA | GGG | CAA | AGT | ATT | ACA | CTA | TAT | TAT | GTT | GAT | AGA | CTT | GGC | TAC | 645 |
| Ile | Thr | Gly | Gln | Ser | Ile | Thr | Leu | Tyr | Tyr | Val | Asp | Arg | Leu | Gly | Tyr | |
| | | | | 85 | | | | | 90 | | | | | 95 | | |
| TAT | CCT | TAC | ATA | GAT | CCT | CAC | ACA | GGT | GCG | ATT | GTG | CAT | GGA | GGA | CTC | 693 |
| Tyr | Pro | Tyr | Ile | Asp | Pro | His | Thr | Gly | Ala | Ile | Val | His | Gly | Gly | Leu | |
| | | | 100 | | | | | 105 | | | | | 110 | | | |
| CCC | CAG | TTG | ATG | AAT | TTA | CAA | CAG | CAT | TTG | AGA | AAA | TCA | AGG | CAA | GAC | 741 |
| Pro | Gln | Leu | Met | Asn | Leu | Gln | Gln | His | Leu | Arg | Lys | Ser | Arg | Gln | Asp | |
| | 115 | | | | | 120 | | | | | 125 | | | | | |
| ATT | TTA | TTT | TAC | ATG | CCC | ACA | GAC | AGC | GTG | GGC | TTG | GCT | GTC | ATT | GAC | 789 |
| Ile | Leu | Phe | Tyr | Met | Pro | Thr | Asp | Ser | Val | Gly | Leu | Ala | Val | Ile | Asp | |
| 130 | | | | | 135 | | | | | 140 | | | | | 145 | |
| TGG | GAA | GAG | TGG | AGG | CCC | ACC | TGG | ACA | AGA | AAC | TGG | AGA | CCT | AAG | GAT | 837 |
| Trp | Glu | Glu | Trp | Arg | Pro | Thr | Trp | Thr | Arg | Asn | Trp | Arg | Pro | Lys | Asp | |
| | | | | 150 | | | | | 155 | | | | | 160 | | |
| ATT | TAC | AGG | AAT | AAA | TCT | ATT | GAG | TTG | GTT | AAG | AGC | CAG | CAT | CCA | CAG | 885 |
| Ile | Tyr | Arg | Asn | Lys | Ser | Ile | Glu | Leu | Val | Lys | Ser | Gln | His | Pro | Gln | |
| | | | 165 | | | | | 170 | | | | | 175 | | | |
| TAT | AAT | CAC | TCA | TAT | GCT | GTT | GCC | GTA | GCC | AAA | AGA | GAC | TTT | GAA | AGG | 933 |
| Tyr | Asn | His | Ser | Tyr | Ala | Val | Ala | Val | Ala | Lys | Arg | Asp | Phe | Glu | Arg | |
| | | | 180 | | | | | 185 | | | | | 190 | | | |
| ACA | GGG | AAG | GCT | TTC | ATG | CTA | GAA | ACT | TTA | AAA | CTG | GGA | AAA | TCA | CTT | 981 |
| Thr | Gly | Lys | Ala | Phe | Met | Leu | Glu | Thr | Leu | Lys | Leu | Gly | Lys | Ser | Leu | |
| | 195 | | | | | 200 | | | | | 205 | | | | | |
| AGG | CCA | AGT | AGC | TTA | TGG | GGT | TAT | TAT | CTT | TTT | CCT | GAT | TGC | TAC | AAC | 1029 |
| Arg | Pro | Ser | Ser | Leu | Trp | Gly | Tyr | Tyr | Leu | Phe | Pro | Asp | Cys | Tyr | Asn | |
| 210 | | | | | 215 | | | | | 220 | | | | | 225 | |
| ACT | CAT | TTC | ACT | AAA | CCC | AAT | TAT | GAT | GGG | CAT | TGC | CCT | CCT | ATA | GAA | 1077 |
| Thr | His | Phe | Thr | Lys | Pro | Asn | Tyr | Asp | Gly | His | Cys | Pro | Pro | Ile | Glu | |
| | | | | 230 | | | | | 235 | | | | | 240 | | |
| CTG | CAA | AGA | AAT | AAC | GAT | CTC | CAA | TGG | TTG | TGG | AAC | GAC | AGC | ACT | GCC | 1125 |
| Leu | Gln | Arg | Asn | Asn | Asp | Leu | Gln | Trp | Leu | Trp | Asn | Asp | Ser | Thr | Ala | |
| | | | 245 | | | | | 250 | | | | | 255 | | | |
| CTT | TAC | CCA | TCT | GTT | TAT | TTG | ACC | AGT | CGA | GTA | AGA | TCA | TCT | CAA | AAT | 1173 |
| Leu | Tyr | Pro | Ser | Val | Tyr | Leu | Thr | Ser | Arg | Val | Arg | Ser | Ser | Gln | Asn | |
| | | 260 | | | | | 265 | | | | | 270 | | | | |
| GGT | GCA | CTT | TAT | GTT | CGT | AAT | CGT | GTA | CAC | GAG | TCC | ATT | AGG | GTT | TCG | 1221 |
| Gly | Ala | Leu | Tyr | Val | Arg | Asn | Arg | Val | His | Glu | Ser | Ile | Arg | Val | Ser | |
| | 275 | | | | | 280 | | | | | 285 | | | | | |
| AAA | CTC | ATG | GAT | GAC | AAA | AAC | CCA | CTT | CCG | ATT | TAT | GTG | TAT | ATC | CGC | 1269 |
| Lys | Leu | Met | Asp | Asp | Lys | Asn | Pro | Leu | Pro | Ile | Tyr | Val | Tyr | Ile | Arg | |
| 290 | | | | | 295 | | | | | 300 | | | | | 305 | |
| CTC | GTT | TTT | ACC | GAT | CAA | ACT | ACT | ACA | TTC | CTT | GAA | CTG | GAT | GAT | CTT | 1317 |
| Leu | Val | Phe | Thr | Asp | Gln | Thr | Thr | Thr | Phe | Leu | Glu | Leu | Asp | Asp | Leu | |
| | | | | 310 | | | | | 315 | | | | | 320 | | |
| GTG | CAT | TCA | GTT | GGC | GAA | ATT | GTT | CCT | CTA | GGT | GTC | TCT | GGA | ATA | ATA | 1365 |
| Val | His | Ser | Val | Gly | Glu | Ile | Val | Pro | Leu | Gly | Val | Ser | Gly | Ile | Ile | |
| | | | 325 | | | | | 330 | | | | | 335 | | | |

| | | | | | | | | | | | | | | | |
|---|---|---|---|---|---|---|---|---|---|---|---|---|---|---|---|
| ATA | TGG | GGA | AGT | CTT | AGT | TTA | ACA | CGA | AGT | TTG | GTT | TCT | TGT | ATA | GGA | 1413 |
| Ile | Trp | Gly | Ser | Leu | Ser | Leu | Thr | Arg | Ser | Leu | Val | Ser | Cys | Ile | Gly |
|     |     | 340 |     |     |     |     | 345 |     |     |     |     | 350 |     |     |     |

| CTA | GAA | AAT | TAC | ATG | AAG | GGT | ACA | CTC | CTG | CCT | TAC | TTA | ATC | AAT | GTC | 1461 |
| Leu | Glu | Asn | Tyr | Met | Lys | Gly | Thr | Leu | Leu | Pro | Tyr | Leu | Ile | Asn | Val |
|     | 355 |     |     |     |     | 360 |     |     |     |     | 365 |     |     |     |     |

| ACC | CTA | GCA | GCC | AAA | ATG | TGT | GGC | CAA | GTG | CTT | TGT | AAG | AAT | CAA | GGA | 1509 |
| Thr | Leu | Ala | Ala | Lys | Met | Cys | Gly | Gln | Val | Leu | Cys | Lys | Asn | Gln | Gly |
| 370 |     |     |     |     | 375 |     |     |     |     | 380 |     |     |     |     | 385 |

| ATT | TGC | ACA | AGG | AAA | GAC | TGG | AAC | ACA | AAC | ACC | TAT | CTT | CAC | CTA | AAC | 1557 |
| Ile | Cys | Thr | Arg | Lys | Asp | Trp | Asn | Thr | Asn | Thr | Tyr | Leu | His | Leu | Asn |
|     |     |     |     | 390 |     |     |     |     | 395 |     |     |     |     | 400 |     |

| GCA | ACA | AAT | TTT | GAC | ATT | GAA | CTT | CAG | CAA | AAT | GGG | AAG | TTT | GTA | GTA | 1605 |
| Ala | Thr | Asn | Phe | Asp | Ile | Glu | Leu | Gln | Gln | Asn | Gly | Lys | Phe | Val | Val |
|     |     |     |     | 405 |     |     |     |     | 410 |     |     |     |     | 415 |     |

| CAT | GGA | AAA | CCA | TCA | CTT | GAA | GAC | CTG | CAG | GAA | TTT | TCC | AAA | AAT | TTT | 1653 |
| His | Gly | Lys | Pro | Ser | Leu | Glu | Asp | Leu | Gln | Glu | Phe | Ser | Lys | Asn | Phe |
|     |     | 420 |     |     |     |     | 425 |     |     |     |     | 430 |     |     |     |

| CAT | TGC | TCC | TGT | TAT | ACC | AAT | GTG | GCT | TGT | AAG | GAC | AGA | CTT | GAT | GTA | 1701 |
| His | Cys | Ser | Cys | Tyr | Thr | Asn | Val | Ala | Cys | Lys | Asp | Arg | Leu | Asp | Val |
|     | 435 |     |     |     |     | 440 |     |     |     |     | 445 |     |     |     |     |

| CAT | AAT | GTC | CGT | TCT | GTT | AAT | GTG | TGT | ACT | GCC | AAT | AAT | ATT | TGT | ATA | 1749 |
| His | Asn | Val | Arg | Ser | Val | Asn | Val | Cys | Thr | Ala | Asn | Asn | Ile | Cys | Ile |
| 450 |     |     |     |     | 455 |     |     |     |     | 460 |     |     |     |     | 465 |

| GAT | GCT | GTT | TTA | AAT | TTT | CCA | TCC | CTG | GAT | GAT | GAT | GAT | GAG | CCT | CCC | 1797 |
| Asp | Ala | Val | Leu | Asn | Phe | Pro | Ser | Leu | Asp | Asp | Asp | Asp | Glu | Pro | Pro |
|     |     |     |     | 470 |     |     |     |     | 475 |     |     |     |     | 480 |     |

| ATC | ACA | GAC | GAC | ACG | TCT | CAA | AAT | CAA | GAC | AGC | ATC | TCC | GAC | ATC | ACA | 1845 |
| Ile | Thr | Asp | Asp | Thr | Ser | Gln | Asn | Gln | Asp | Ser | Ile | Ser | Asp | Ile | Thr |
|     |     |     | 485 |     |     |     |     | 490 |     |     |     |     | 495 |     |     |

| TCA | TCT | GCT | CCA | CCG | TCT | TCA | CAT | ATT | CTT | CCA | AAG | GAT | CTC | AGT | TGG | 1893 |
| Ser | Ser | Ala | Pro | Pro | Ser | Ser | His | Ile | Leu | Pro | Lys | Asp | Leu | Ser | Trp |
|     |     | 500 |     |     |     |     | 505 |     |     |     |     | 510 |     |     |     |

| TGC | CTC | TTC | CTT | CTC | TCT | ATC | TTT | TCA | CAG | CAC | TGG | AAA | TAT | TTA | CTA | 1941 |
| Cys | Leu | Phe | Leu | Leu | Ser | Ile | Phe | Ser | Gln | His | Trp | Lys | Tyr | Leu | Leu |
|     | 515 |     |     |     |     | 520 |     |     |     |     | 525 |     |     |     |     |

| TAGGCTCATG | GCAACTGAAA | AGTACCAAAT | TCAATATCAT | AAAAATTCTA | TAATCAAAAT | 2001 |
| CCTTTGAATT | TTTAAAGCAA | AATACATACT | ATTCTATCAA | AGACACTGTA | AAGCCTGTGG | 2061 |
| TACTTGGAAG | ATACAGCTTT | CTTTTGAGAA | GAGTGAAGAT | TTGAATAAAA | CAAAATTACT | 2121 |
| GAAAAAAAAA | AAAAAAAAAA | AAAAAAAAA A | | | | 2152 |

( 2 ) INFORMATION FOR SEQ ID NO:2:

( i ) SEQUENCE CHARACTERISTICS:
        ( A ) LENGTH: 529 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Gly | Ala | Phe | Thr | Phe | Lys | His | Ser | Phe | Phe | Gly | Ser | Phe | Val | Glu |
|---|---|---|---|---|---|---|---|---|---|---|---|---|---|---|---|
| 1 |  |  |  | 5 |  |  |  |  | 10 |  |  |  |  | 15 |  |

| Cys | Ser | Gly | Val | Leu | Gln | Thr | Val | Phe | Ile | Phe | Leu | Leu | Ile | Pro | Cys |
|  |  |  | 20 |  |  |  |  | 25 |  |  |  |  | 30 |  |  |

| Cys | Leu | Ala | Asp | Lys | Arg | Ala | Pro | Leu | Ile | Pro | Asn | Val | Pro | Leu |
|  |  | 35 |  |  |  |  | 40 |  |  |  |  | 45 |  |  |

| Leu | Trp | Val | Trp | Asn | Ala | Pro | Thr | Glu | Phe | Cys | Ile | Gly | Gly | Thr | Asn |
|  | 50 |  |  |  |  | 55 |  |  |  |  | 60 |  |  |  |  |

| | | | | | | | | | | | | | | |
|---|---|---|---|---|---|---|---|---|---|---|---|---|---|---|
| Gln | Pro | Leu | Asp | Met | Ser | Phe | Phe | Ser | Ile | Val | Gly | Thr | Pro | Arg | Lys |
| 65 | | | | | 70 | | | | 75 | | | | | 80 |
| Asn | Ile | Thr | Gly | Gln | Ser | Ile | Thr | Leu | Tyr | Tyr | Val | Asp | Arg | Leu | Gly |
| | | | | 85 | | | | | 90 | | | | | 95 | |
| Tyr | Tyr | Pro | Tyr | Ile | Asp | Pro | His | Thr | Gly | Ala | Ile | Val | His | Gly | Gly |
| | | | 100 | | | | | 105 | | | | | 110 | | |
| Leu | Pro | Gln | Leu | Met | Asn | Leu | Gln | Gln | His | Leu | Arg | Lys | Ser | Arg | Gln |
| | | | 115 | | | | | 120 | | | | 125 | | | |
| Asp | Ile | Leu | Phe | Tyr | Met | Pro | Thr | Asp | Ser | Val | Gly | Leu | Ala | Val | Ile |
| | 130 | | | | | 135 | | | | | 140 | | | | |
| Asp | Trp | Glu | Glu | Trp | Arg | Pro | Thr | Trp | Thr | Arg | Asn | Trp | Arg | Pro | Lys |
| 145 | | | | | 150 | | | | | 155 | | | | | 160 |
| Asp | Ile | Tyr | Arg | Asn | Lys | Ser | Ile | Glu | Leu | Val | Lys | Ser | Gln | His | Pro |
| | | | | 165 | | | | | 170 | | | | | 175 | |
| Gln | Tyr | Asn | His | Ser | Tyr | Ala | Val | Ala | Val | Ala | Lys | Arg | Asp | Phe | Glu |
| | | | 180 | | | | | 185 | | | | | 190 | | |
| Arg | Thr | Gly | Lys | Ala | Phe | Met | Leu | Glu | Thr | Leu | Lys | Leu | Gly | Lys | Ser |
| | | 195 | | | | | 200 | | | | | 205 | | | |
| Leu | Arg | Pro | Ser | Ser | Leu | Trp | Gly | Tyr | Tyr | Leu | Phe | Pro | Asp | Cys | Tyr |
| | 210 | | | | | 215 | | | | | 220 | | | | |
| Asn | Thr | His | Phe | Thr | Lys | Pro | Asn | Tyr | Asp | Gly | His | Cys | Pro | Pro | Ile |
| 225 | | | | | 230 | | | | | 235 | | | | | 240 |
| Glu | Leu | Gln | Arg | Asn | Asn | Asp | Leu | Gln | Trp | Leu | Trp | Asn | Asp | Ser | Thr |
| | | | | 245 | | | | | 250 | | | | | 255 | |
| Ala | Leu | Tyr | Pro | Ser | Val | Tyr | Leu | Thr | Ser | Arg | Val | Arg | Ser | Ser | Gln |
| | | | 260 | | | | | 265 | | | | | 270 | | |
| Asn | Gly | Ala | Leu | Tyr | Val | Arg | Asn | Arg | Val | His | Glu | Ser | Ile | Arg | Val |
| | | | 275 | | | | | 280 | | | | | 285 | | |
| Ser | Lys | Leu | Met | Asp | Asp | Lys | Asn | Pro | Leu | Pro | Ile | Tyr | Val | Tyr | Ile |
| | 290 | | | | | 295 | | | | | 300 | | | | |
| Arg | Leu | Val | Phe | Thr | Asp | Gln | Thr | Thr | Thr | Phe | Leu | Glu | Leu | Asp | Asp |
| 305 | | | | | 310 | | | | | 315 | | | | | 320 |
| Leu | Val | His | Ser | Val | Gly | Glu | Ile | Val | Pro | Leu | Gly | Val | Ser | Gly | Ile |
| | | | | 325 | | | | | 330 | | | | | 335 | |
| Ile | Ile | Trp | Gly | Ser | Leu | Ser | Leu | Thr | Arg | Ser | Leu | Val | Ser | Cys | Ile |
| | | | 340 | | | | | 345 | | | | | 350 | | |
| Gly | Leu | Glu | Asn | Tyr | Met | Lys | Gly | Thr | Leu | Leu | Pro | Tyr | Leu | Ile | Asn |
| | | | 355 | | | | | 360 | | | | 365 | | | |
| Val | Thr | Leu | Ala | Ala | Lys | Met | Cys | Gly | Gln | Val | Leu | Cys | Lys | Asn | Gln |
| | | | 370 | | | | 375 | | | | | 380 | | | |
| Gly | Ile | Cys | Thr | Arg | Lys | Asp | Trp | Asn | Thr | Asn | Thr | Tyr | Leu | His | Leu |
| 385 | | | | | 390 | | | | | 395 | | | | | 400 |
| Asn | Ala | Thr | Asn | Phe | Asp | Ile | Glu | Leu | Gln | Gln | Asn | Gly | Lys | Phe | Val |
| | | | | 405 | | | | | 410 | | | | | 415 | |
| Val | His | Gly | Lys | Pro | Ser | Leu | Glu | Asp | Leu | Gln | Glu | Phe | Ser | Lys | Asn |
| | | | 420 | | | | | 425 | | | | | 430 | | |
| Phe | His | Cys | Ser | Cys | Tyr | Thr | Asn | Val | Ala | Cys | Lys | Asp | Arg | Leu | Asp |
| | | | 435 | | | | | 440 | | | | 445 | | | |
| Val | His | Asn | Val | Arg | Ser | Val | Asn | Val | Cys | Thr | Ala | Asn | Asn | Ile | Cys |
| | | | 450 | | | | 455 | | | | | 460 | | | |
| Ile | Asp | Ala | Val | Leu | Asn | Phe | Pro | Ser | Leu | Asp | Asp | Asp | Glu | Pro |
| 465 | | | | | 470 | | | | | 475 | | | | | 480 |
| Pro | Ile | Thr | Asp | Asp | Thr | Ser | Gln | Asn | Gln | Asp | Ser | Ile | Ser | Asp | Ile |

|     | 485 |     |     |     |     | 490 |     |     |     |     | 495 |     |     |
|-----|-----|-----|-----|-----|-----|-----|-----|-----|-----|-----|-----|-----|-----|

Thr Ser Ser Ala Pro Pro Ser Ser His Ile Leu Pro Lys Asp Leu Ser
            500                 505             510

Trp Cys Leu Phe Leu Leu Ser Ile Phe Ser Gln His Trp Lys Tyr Leu
        515                 520             525

Leu ( 2 ) INFORMATION FOR SEQ ID NO:3:

( i ) SEQUENCE CHARACTERISTICS:
        ( A ) LENGTH: 2125 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 313..1848

( x i ) SEQUENCE DESCRIPTION: SEQ ID NO:3:

```
CTAAGAGTGC TGAAGTAGAT TTAGATTGAC CATGGCTCAC ATGAATTAAG AAGTGTTTTC        60

TTTTGTTATG ATGGAGATGC GAGTGGTAGG CAGGTATTTT AAGTTTCCAG CAAGTTCTGG       120

ATGATTTAAC TTGCTCCAAG ATATTCCTGA AATGTAACAC AGGAAGAAGA ATCTTCAGTG       180

TAAATCAGTC ACCATACATT CATCTCCCTC AATAGCCTCA TGCCACAGTC TTTCTAATCT       240

TTTGCATCTA ATACTAAACA GACCACAGTG TGTAAGAAGG AATAAGTGCC TACTTAGTAA       300

TTATTCTCTG TG ATG GGA GAG TTG AGA TTT AAG CAC CTC TTT TGG GGG          348
              Met Gly Glu Leu Arg Phe Lys His Leu Phe Trp Gly
                1               5                  10

AGC TTT GTT GAA CTC GGG GGC ACA TTC CAA ACA GTG TTA ATC TTC CTT        396
Ser Phe Val Glu Leu Gly Gly Thr Phe Gln Thr Val Leu Ile Phe Leu
        15                  20                  25

TTG ATT CCA TGC TCC TTG ACT GTG GAT TAT AGG GCA GCA CCA ATT TTA        444
Leu Ile Pro Cys Ser Leu Thr Val Asp Tyr Arg Ala Ala Pro Ile Leu
    30                  35                  40

TCA AAT ACA ACT TTC CTT TGG ATT TGG AAT GTC CCA ACT GAA CGT TGT        492
Ser Asn Thr Thr Phe Leu Trp Ile Trp Asn Val Pro Thr Glu Arg Cys
 45                 50                  55                  60

GTA GGA AAT GTT AAT GAT CCA ATA GAT CTG AGC TTC TTC TCT TTA ATT        540
Val Gly Asn Val Asn Asp Pro Ile Asp Leu Ser Phe Phe Ser Leu Ile
                65                  70                  75

GGA AGC CCC CGG AAA ACT GCC ACA GGG CAA CCT GTC ACA TTA TTT TAT        588
Gly Ser Pro Arg Lys Thr Ala Thr Gly Gln Pro Val Thr Leu Phe Tyr
            80                  85                  90

GTT GAT CGA CTT GGT TTG TAT CCT CAC ATA GAT GCA AAC CAA GCA GAA        636
Val Asp Arg Leu Gly Leu Tyr Pro His Ile Asp Ala Asn Gln Ala Glu
        95                  100                 105

CAT TAT GGA GGA ATA CCT CAG AGG GGC GAT TAT CAA GCT CAT TTG CGC        684
His Tyr Gly Gly Ile Pro Gln Arg Gly Asp Tyr Gln Ala His Leu Arg
    110                 115                 120

AAA GCT AAG ACT GAC ATA GAG CAT TAC ATT CCA GAC GAC AAA TTG GGC        732
Lys Ala Lys Thr Asp Ile Glu His Tyr Ile Pro Asp Asp Lys Leu Gly
125                 130                 135                 140

TTA GCT ATC ATT GAC TGG GAA GAA TGG AGG CCT ACC TGG TTG AGA AAC        780
Leu Ala Ile Ile Asp Trp Glu Glu Trp Arg Pro Thr Trp Leu Arg Asn
                145                 150                 155

TGG AAA CCT AAG GAT AAC TAC AGG AAT AAG TCT ATT GAA TTG GTC CAA        828
Trp Lys Pro Lys Asp Asn Tyr Arg Asn Lys Ser Ile Glu Leu Val Gln
            160                 165                 170

TCA ACT AAT CCA GGA CTT AGT ATC ACA AGA GCC ACC CAG AAA GCC ATA        876
```

```
                Ser Thr Asn Pro Gly Leu Ser Ile Thr Arg Ala Thr Gln Lys Ala Ile
                        175                 180                 185

CAA CAA CTT GAA GAG GCA GGA AGG AAG TTT ATG GAA GGA ACT TTA CAC         924
Gln Gln Leu Glu Glu Ala Gly Arg Lys Phe Met Glu Gly Thr Leu His
        190                 195                 200

CTG GGG AAA TTC CTT CGA CCA AAC CAG CTA TGG GGT TAT TAT CTA TTT         972
Leu Gly Lys Phe Leu Arg Pro Asn Gln Leu Trp Gly Tyr Tyr Leu Phe
205                 210                 215                 220

CCT GAT TGT TAT AAC AAT AAG TTT CAA GAC CCT AAG TAT GAT GGG CAG        1020
Pro Asp Cys Tyr Asn Asn Lys Phe Gln Asp Pro Lys Tyr Asp Gly Gln
                225                 230                 235

TGC CCT GCT GTG GAA AAG AAA AGA AAT GAT AAT CTT AAA TGG CTA TGG        1068
Cys Pro Ala Val Glu Lys Lys Arg Asn Asp Asn Leu Lys Trp Leu Trp
                240                 245                 250

AAA GCA AGC ACC GGC CTT TAC CCA TCT GTC TAT TTG AAG AAA GAC TTG        1116
Lys Ala Ser Thr Gly Leu Tyr Pro Ser Val Tyr Leu Lys Lys Asp Leu
        255                 260                 265

AAG TCC AAT CGA CAA GCT ACC CTC TAT GTC CGC TAC CGA GTT GTG GAA        1164
Lys Ser Asn Arg Gln Ala Thr Leu Tyr Val Arg Tyr Arg Val Val Glu
        270                 275                 280

GCT ATC AGA GTG TCC AAG GTT GGG AAT GCA TCG GAT CCA GTC CCG ATT        1212
Ala Ile Arg Val Ser Lys Val Gly Asn Ala Ser Asp Pro Val Pro Ile
285                 290                 295                 300

TTT GTC TAT ATC CGT CTT GTT TTT ACT GAT CGT ACC TCT GAA TAC CTT        1260
Phe Val Tyr Ile Arg Leu Val Phe Thr Asp Arg Thr Ser Glu Tyr Leu
                305                 310                 315

CTA GAG GAT GAC CTT GTG AAT ACA ATT GGT GAA ATT GTT GCT CTG GGT        1308
Leu Glu Asp Asp Leu Val Asn Thr Ile Gly Glu Ile Val Ala Leu Gly
                320                 325                 330

ACC TCT GGA ATT ATA ATA TGG GAT GCT ATG AGT TTA GCA CAA CGT GCG        1356
Thr Ser Gly Ile Ile Ile Trp Asp Ala Met Ser Leu Ala Gln Arg Ala
        335                 340                 345

GCA GGT TGC CCA ATC CTA CAT AAA TAC ATG CAG ACG ACC CTG AAT CCA        1404
Ala Gly Cys Pro Ile Leu His Lys Tyr Met Gln Thr Thr Leu Asn Pro
350                 355                 360

TAC ATA GTC AAT GTT ACC CTA GCA GCC AAA ATG TGC AGC CAA ACA CTT        1452
Tyr Ile Val Asn Val Thr Leu Ala Ala Lys Met Cys Ser Gln Thr Leu
365                 370                 375                 380

TGT AAT GAG AAA GGC ATG TGT TCA AGA AGA AAA GAA AGT TCA GAT GTA        1500
Cys Asn Glu Lys Gly Met Cys Ser Arg Arg Lys Glu Ser Ser Asp Val
                385                 390                 395

TAT CTT CAC TTG AAC CCA AGT CAT TTT GAT ATT ATG TTA ACG CAA ACT        1548
Tyr Leu His Leu Asn Pro Ser His Phe Asp Ile Met Leu Thr Gln Thr
                400                 405                 410

GGA AAG TAC GAA GTT CTT GGC AAC CCC AGG GTT GGA GAC TTA GAA TAC        1596
Gly Lys Tyr Glu Val Leu Gly Asn Pro Arg Val Gly Asp Leu Glu Tyr
        415                 420                 425

TTT TCT GAA CAT TTT AAA TGC AGC TGT TTT AGC AGA ATG ACA TGT AAG        1644
Phe Ser Glu His Phe Lys Cys Ser Cys Phe Ser Arg Met Thr Cys Lys
        430                 435                 440

GAG ACA TCT GAT GTA AAA AAT GTA CAA GAC GTG AAT GTG TGC GTC GGT        1692
Glu Thr Ser Asp Val Lys Asn Val Gln Asp Val Asn Val Cys Val Gly
445                 450                 455                 460

GAC AAT GTT TGT ATA AAA GCC AAG GTA GAA CCC AAC CCA GCC TTC TAC        1740
Asp Asn Val Cys Ile Lys Ala Lys Val Glu Pro Asn Pro Ala Phe Tyr
                465                 470                 475

CTC CTA CCT GGC AAA AGC CTT CTA TTT ATG ACA ACA CTT GGT CAT GTG        1788
Leu Leu Pro Gly Lys Ser Leu Leu Phe Met Thr Thr Leu Gly His Val
                480                 485                 490

CTG TAC CAT CTG CCA CAA GAT ATT TTT GTT TTT CCA CGG AAG ACA CTA        1836
```

|     | Leu | Tyr | His | Leu | Pro | Gln | Asp | Ile | Phe | Val | Phe | Pro | Arg | Lys | Thr | Leu |     |
|-----|-----|-----|-----|-----|-----|-----|-----|-----|-----|-----|-----|-----|-----|-----|-----|-----|-----|
|     |     |     | 495 |     |     |     | 500 |     |     |     |     |     | 505 |     |     |     |     |

```
GTC AGT ACT CCT TAGTTTCTC TACCCACAGC GTTGATGTA TTATTATTAT                   1888
Val Ser Thr Pro
        510

TATTTTTGCA GGCCTCAGTA ATTTGGGATT ATGAATGGGA TTCTATTTTA CCAAAGTAAT          1948

TCAATTTTTA TAATCAAGAT TCTATTTTTG AGTTCAAAG AGAAATTATA TATTCTTCTA          2008

CCAAAGATTG ATTACAAGCA AGGCTACTTA GGGATTAGTT TTGGTTTAAA GAGAATGAAG          2068

ACTGAATAAA ATAAAATCAC TAGAAAATTA AAAAAAAAAA AAAAAAAAAA AAAAAA             2125
```

( 2 ) INFORMATION FOR SEQ ID NO:4:

( i ) SEQUENCE CHARACTERISTICS:
( A ) LENGTH: 512 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met Gly Glu Leu Arg Phe Lys His Leu Phe Trp Gly Ser Phe Val Glu
 1               5                  10                 15

Leu Gly Gly Thr Phe Gln Thr Val Leu Ile Phe Leu Leu Ile Pro Cys
            20                  25                 30

Ser Leu Thr Val Asp Tyr Arg Ala Ala Pro Ile Leu Ser Asn Thr Thr
        35                  40                 45

Phe Leu Trp Ile Trp Asn Val Pro Thr Glu Arg Cys Val Gly Asn Val
    50                  55                 60

Asn Asp Pro Ile Asp Leu Ser Phe Phe Ser Leu Ile Gly Ser Pro Arg
65                  70                 75                      80

Lys Thr Ala Thr Gly Gln Pro Val Thr Leu Phe Tyr Val Asp Arg Leu
            85                  90                 95

Gly Leu Tyr Pro His Ile Asp Ala Asn Gln Ala Glu His Tyr Gly Gly
            100                 105                110

Ile Pro Gln Arg Gly Asp Tyr Gln Ala His Leu Arg Lys Ala Lys Thr
            115                 120                125

Asp Ile Glu His Tyr Ile Pro Asp Asp Lys Leu Gly Leu Ala Ile Ile
130                 135                140

Asp Trp Glu Glu Trp Arg Pro Thr Trp Leu Arg Asn Trp Lys Pro Lys
145                 150                155                     160

Asp Asn Tyr Arg Asn Lys Ser Ile Glu Leu Val Gln Ser Thr Asn Pro
            165                170                 175

Gly Leu Ser Ile Thr Arg Ala Thr Gln Lys Ala Ile Gln Gln Leu Glu
            180                185                 190

Glu Ala Gly Arg Lys Phe Met Glu Gly Thr Leu His Leu Gly Lys Phe
            195                200                 205

Leu Arg Pro Asn Gln Leu Trp Gly Tyr Tyr Leu Phe Pro Asp Cys Tyr
    210                 215                 220

Asn Asn Lys Phe Gln Asp Pro Lys Tyr Asp Gly Gln Cys Pro Ala Val
225                 230                 235                 240

Glu Lys Lys Arg Asn Asp Asn Leu Lys Trp Leu Trp Lys Ala Ser Thr
            245                 250                 255

Gly Leu Tyr Pro Ser Val Tyr Leu Lys Lys Asp Leu Lys Ser Asn Arg
            260                 265                 270

Gln Ala Thr Leu Tyr Val Arg Tyr Arg Val Val Glu Ala Ile Arg Val
            275                 280                 285
```

| | | | | | | | | | | | | | | |
|---|---|---|---|---|---|---|---|---|---|---|---|---|---|---|
|Ser|Lys<br>290|Val|Gly|Asn|Ala|Ser<br>295|Asp|Pro|Val|Pro<br>300|Ile|Phe|Val|Tyr|Ile|
|Arg<br>305|Leu|Val|Phe|Thr|Asp<br>310|Arg|Thr|Ser|Glu|Tyr<br>315|Leu|Leu|Glu|Asp|Asp<br>320|
|Leu|Val|Asn|Thr|Ile<br>325|Gly|Glu|Ile|Val|Ala<br>330|Leu|Gly|Thr|Ser|Gly<br>335|Ile|
|Ile|Ile|Trp|Asp<br>340|Ala|Met|Ser|Leu|Ala|Gln<br>345|Arg|Ala|Ala|Gly<br>350|Cys|Pro|
|Ile|Leu|His<br>355|Lys|Tyr|Met|Gln|Thr<br>360|Thr|Leu|Asn|Pro|Tyr<br>365|Ile|Val|Asn|
|Val|Thr<br>370|Leu|Ala|Ala|Lys|Met<br>375|Cys|Ser|Gln|Thr|Leu<br>380|Cys|Asn|Glu|Lys|
|Gly<br>385|Met|Cys|Ser|Arg|Arg<br>390|Lys|Glu|Ser|Ser|Asp<br>395|Val|Tyr|Leu|His|Leu<br>400|
|Asn|Pro|Ser|His|Phe<br>405|Asp|Ile|Met|Leu|Thr<br>410|Gln|Thr|Gly|Lys|Tyr<br>415|Glu|
|Val|Leu|Gly|Asn<br>420|Pro|Arg|Val|Gly|Asp<br>425|Leu|Glu|Tyr|Phe|Ser<br>430|Glu|His|
|Phe|Lys|Cys<br>435|Ser|Cys|Phe|Ser|Arg<br>440|Met|Thr|Cys|Lys|Glu<br>445|Thr|Ser|Asp|
|Val|Lys|Asn<br>450|Val|Gln|Asp|Val<br>455|Asn|Val|Cys|Val|Gly<br>460|Asp|Asn|Val|Cys|
|Ile|Lys<br>465|Ala|Lys|Val|Glu|Pro<br>470|Asn|Pro|Ala|Phe<br>475|Tyr|Leu|Leu|Pro|Gly<br>480|
|Lys|Ser|Leu|Leu|Phe<br>485|Met|Thr|Thr|Leu|Gly<br>490|His|Val|Leu|Tyr|His<br>495|Leu|
|Pro|Gln|Asp|Ile<br>500|Phe|Val|Phe|Pro|Arg<br>505|Lys|Thr|Leu|Val|Ser<br>510|Thr|Pro|

( 2 ) INFORMATION FOR SEQ ID NO:5:

( i ) SEQUENCE CHARACTERISTICS:
        ( A ) LENGTH: 1695 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 109..1635

( x i ) SEQUENCE DESCRIPTION: SEQ ID NO:5:

```
GGAATTCATT CCATTCCCTT TCATCTGTGC TCATACTTTG CATCAGATAT TGGGTAAACC      60

AAAGTGTGTA GGAAGAAATA AATGTTTCA TAGTCATTAC TCTTTACA ATG GGA GTG       117
                                                    Met Gly Val
                                                     1
```

| | | | | | | | | | | | | | | | | |
|---|---|---|---|---|---|---|---|---|---|---|---|---|---|---|---|---|
|CTA|AAA|TTC|AAG|CAC|ATC|TTT|TTC|AGA|AGC|TTT|GTT|AAA|TCA|AGT|GGA| 165|
|Leu|Lys<br>5|Phe|Lys|His|Ile<br>10|Phe|Phe|Arg|Ser|Phe<br>15|Val|Lys|Ser|Ser|Gly| |
|GTA|TCC|CAG|ATA|GTT|TTC|ACC|TTC|CTT|CTG|ATT|CCA|TGT|TGC|TTG|ACT| 213|
|Val<br>20|Ser|Gln|Ile|Val|Phe<br>25|Thr|Phe|Leu|Leu|Ile<br>30|Pro|Cys|Cys|Leu|Thr<br>35| |
|CTG|AAT|TTC|AGA|GCA|CCT|CCT|GTT|ATT|CCA|AAT|GTG|CCT|TTC|CTC|TGG| 261|
|Leu|Asn|Phe|Arg|Ala<br>40|Pro|Pro|Val|Ile|Pro<br>45|Asn|Val|Pro|Phe|Leu<br>50|Trp| |
|GCC|TGG|AAT|GCC|CCA|AGT|GAA|TTT|TGT|CTT|GGA|AAA|TTT|GAT|GAG|CCA| 309|
|Ala|Trp|Asn|Ala|Pro<br>55|Ser|Glu|Phe|Cys|Leu<br>60|Gly|Lys|Phe|Asp|Glu<br>65|Pro| |

| | | | | | | | | | | | | | | | | |
|---|---|---|---|---|---|---|---|---|---|---|---|---|---|---|---|---|
| CTA | GAT | ATG | AGC | CTC | TTC | TCT | TTC | ATA | GGA | AGC | CCC | CGA | ATA | AAC | GCC | 357 |
| Leu | Asp | Met 70 | Ser | Leu | Phe | Ser | Phe 75 | Ile | Gly | Ser | Pro | Arg 80 | Ile | Asn | Ala | |
| ACC | GGG | CAA | GGA | GTT | ACA | ATA | TTT | TAT | GTT | GAT | AGA | CTT | GGC | TAC | TAT | 405 |
| Thr | Gly | Gln 85 | Gly | Val | Thr | Ile | Phe 90 | Tyr | Val | Asp | Arg 95 | Leu | Gly | Tyr | Tyr | |
| CCT | TAC | ATA | GAT | TCA | ATC | ACA | GGA | GTA | ACT | GTG | AAT | GGA | GGA | ATC | CCC | 453 |
| Pro 100 | Tyr | Ile | Asp | Ser | Ile 105 | Thr | Gly | Val | Thr | Val 110 | Asn | Gly | Gly | Ile | Pro 115 | |
| CAG | AAG | ATT | TCC | TTA | CAA | GAC | CAT | CTG | GAC | AAA | GCT | AAG | AAA | GAC | ATT | 501 |
| Gln | Lys | Ile | Ser | Leu 120 | Gln | Asp | His | Leu | Asp 125 | Lys | Ala | Lys | Lys | Asp 130 | Ile | |
| ACA | TTT | TAT | ATG | CCA | GTA | GAC | AAT | TTG | GGA | ATG | GCT | GTT | ATT | GAC | TGG | 549 |
| Thr | Phe | Tyr | Met 135 | Pro | Val | Asp | Asn | Leu 140 | Gly | Met | Ala | Val | Ile 145 | Asp | Trp | |
| GAA | GAA | TGG | AGA | CCC | ACT | TGG | GCA | AGA | AAC | TGG | AAA | CCT | AAA | GAT | GTT | 597 |
| Glu | Glu | Trp | Arg 150 | Pro | Thr | Trp | Ala | Arg 155 | Asn | Trp | Lys | Pro | Lys 160 | Asp | Val | |
| TAC | AAG | AAT | AGG | TCT | ATT | GAA | TTG | GTT | CAG | CAA | CAA | AAT | GTA | CAA | CTT | 645 |
| Tyr | Lys 165 | Asn | Arg | Ser | Ile | Glu 170 | Leu | Val | Gln | Gln | Gln 175 | Asn | Val | Gln | Leu | |
| AGT | CTC | ACA | GAG | GCC | ACT | GAG | AAA | GCA | AAA | CAA | GAA | TTT | GAA | AAG | GCA | 693 |
| Ser 180 | Leu | Thr | Glu | Ala | Thr 185 | Glu | Lys | Ala | Lys | Gln 190 | Glu | Phe | Glu | Lys | Ala 195 | |
| GGG | AAG | GAT | TTC | CTG | GTA | GAG | ACT | ATA | AAA | TTG | GGA | AAA | TTA | CTT | CGG | 741 |
| Gly | Lys | Asp | Phe | Leu 200 | Val | Glu | Thr | Ile | Lys 205 | Leu | Gly | Lys | Leu | Leu 210 | Arg | |
| CCA | AAT | CAC | TTG | TGG | GGT | TAT | TAT | CTT | TTT | CCG | GAT | TGT | TAC | AAC | CAT | 789 |
| Pro | Asn | His | Leu 215 | Trp | Gly | Tyr | Tyr | Leu 220 | Phe | Pro | Asp | Cys | Tyr 225 | Asn | His | |
| CAC | TAT | AAG | AAA | CCC | GGT | TAC | AAT | GGA | AGT | TGC | TTC | AAT | GTA | GAA | ATA | 837 |
| His | Tyr | Lys 230 | Lys | Pro | Gly | Tyr | Asn 235 | Gly | Ser | Cys | Phe | Asn 240 | Val | Glu | Ile | |
| AAA | AGA | AAT | GAT | GAT | CTC | AGC | TGG | TTG | TGG | AAT | GAA | AGC | ACT | GCT | CTT | 885 |
| Lys | Arg 245 | Asn | Asp | Asp | Leu | Ser 250 | Trp | Leu | Trp | Asn | Glu 255 | Ser | Thr | Ala | Leu | |
| TAC | CCA | TCC | ATT | TAT | TTG | AAC | ACT | CAG | CAG | TCT | CCT | GTA | GCT | GCT | ACA | 933 |
| Tyr 260 | Pro | Ser | Ile | Tyr | Leu 265 | Asn | Thr | Gln | Gln | Ser 270 | Pro | Val | Ala | Ala | Thr 275 | |
| CTC | TAT | GTG | CGC | AAT | CGA | GTT | CGG | GAA | GCC | ATC | AGA | GTT | TCC | AAA | ATA | 981 |
| Leu | Tyr | Val | Arg | Asn 280 | Arg | Val | Arg | Glu | Ala 285 | Ile | Arg | Val | Ser | Lys 290 | Ile | |
| CCT | GAT | GCA | AAA | AGT | CCA | CTT | CCG | GTT | TTT | GCA | TAT | ACC | CGC | ATA | GTT | 1029 |
| Pro | Asp | Ala | Lys 295 | Ser | Pro | Leu | Pro | Val 300 | Phe | Ala | Tyr | Thr | Arg 305 | Ile | Val | |
| TTT | ACT | GAT | CAA | GTT | TTG | AAA | TTC | CTT | TCT | CAA | GAT | GAA | CTT | GTG | TAT | 1077 |
| Phe | Thr | Asp | Gln 310 | Val | Leu | Lys | Phe | Leu 315 | Ser | Gln | Asp | Glu | Leu 320 | Val | Tyr | |
| ACA | TTT | GGC | GAA | ACT | GTT | GCT | CTG | GGT | GCT | TCT | GGA | ATT | GTA | ATA | TGG | 1125 |
| Thr | Phe | Gly 325 | Glu | Thr | Val | Ala | Leu 330 | Gly | Ala | Ser | Gly | Ile 335 | Val | Ile | Trp | |
| GGA | ACC | CTC | AGT | ATA | ATG | CGA | AGT | ATG | AAA | TCT | TGC | TTG | CTC | CTA | GAC | 1173 |
| Gly 340 | Thr | Leu | Ser | Ile | Met 345 | Arg | Ser | Met | Lys | Ser 350 | Cys | Leu | Leu | Leu | Asp 355 | |
| AAT | TAC | ATG | GAG | ACT | ATA | CTG | AAT | CCT | TAC | ATA | ATC | AAC | GTC | ACA | CTA | 1221 |
| Asn | Tyr | Met | Glu | Thr 360 | Ile | Leu | Asn | Pro | Tyr 365 | Ile | Ile | Asn | Val | Thr 370 | Leu | |
| GCA | GCC | AAA | ATG | TGT | AGC | CAA | GTG | CTT | TGC | CAG | GAG | CAA | GGA | GTG | TGT | 1269 |
| Ala | Ala | Lys | Met 375 | Cys | Ser | Gln | Val | Leu 380 | Cys | Gln | Glu | Gln | Gly 385 | Val | Cys | |

| | | | | | | | | | | | | | | | | |
|---|---|---|---|---|---|---|---|---|---|---|---|---|---|---|---|---|
| ATA | AGG | AAA | AAC | TGG | AAT | TCA | AGT | GAC | TAT | CTT | CAC | CTC | AAC | CCA | GAT | 1317 |
| Ile | Arg | Lys | Asn | Trp | Asn | Ser | Ser | Asp | Tyr | Leu | His | Leu | Asn | Pro | Asp | |
| | | 390 | | | | | 395 | | | | | 400 | | | | |
| AAT | TTT | GCT | ATT | CAA | CTT | GAG | AAA | GGT | GGA | AAG | TTC | ACA | GTA | CGT | GGA | 1365 |
| Asn | Phe | Ala | Ile | Gln | Leu | Glu | Lys | Gly | Gly | Lys | Phe | Thr | Val | Arg | Gly | |
| | 405 | | | | | 410 | | | | | 415 | | | | | |
| AAA | CCG | ACA | CTT | GAA | GAC | CTG | GAG | CAA | TTT | TCT | GAA | AAA | TTT | TAT | TGC | 1413 |
| Lys | Pro | Thr | Leu | Glu | Asp | Leu | Glu | Gln | Phe | Ser | Glu | Lys | Phe | Tyr | Cys | |
| 420 | | | | | 425 | | | | | 430 | | | | | 435 | |
| AGC | TGT | TAT | AGC | ACC | TTG | AGT | TGT | AAG | GAG | AAA | GCT | GAT | GTA | AAA | GAC | 1461 |
| Ser | Cys | Tyr | Ser | Thr | Leu | Ser | Cys | Lys | Glu | Lys | Ala | Asp | Val | Lys | Asp | |
| | | | | 440 | | | | | 445 | | | | | 450 | | |
| ACT | GAT | GCT | GTT | GAT | GTG | TGT | ATT | GCT | GAT | GGT | GTC | TGT | ATA | GAT | GCT | 1509 |
| Thr | Asp | Ala | Val | Asp | Val | Cys | Ile | Ala | Asp | Gly | Val | Cys | Ile | Asp | Ala | |
| | | | 455 | | | | | 460 | | | | | 465 | | | |
| TTT | CTA | AAA | CCT | CCC | ATG | GAG | ACA | GAA | GAA | CCT | CAA | ATT | TTC | TAC | AAT | 1557 |
| Phe | Leu | Lys | Pro | Pro | Met | Glu | Thr | Glu | Glu | Pro | Gln | Ile | Phe | Tyr | Asn | |
| | | 470 | | | | | 475 | | | | | 480 | | | | |
| GCT | TCA | CCC | TCC | ACA | CTA | TCT | GCC | ACA | ATG | TTC | ATT | GTT | AGT | ATT | TTG | 1605 |
| Ala | Ser | Pro | Ser | Thr | Leu | Ser | Ala | Thr | Met | Phe | Ile | Val | Ser | Ile | Leu | |
| | 485 | | | | | 490 | | | | | 495 | | | | | |
| TTT | CTT | ATC | ATT | TCT | TCT | GTA | GCG | AGT | TTG | TAATTGCGCA | | GGTTAGCTGA | | | | 1655 |
| Phe | Leu | Ile | Ile | Ser | Ser | Val | Ala | Ser | Leu | | | | | | | |
| 500 | | | | 505 | | | | | | | | | | | | |

AATGAACAAT ATGTCCATCT TAAAGTGTGC TTCCCGAATT 1695

( 2 ) INFORMATION FOR SEQ ID NO:6:

( i ) SEQUENCE CHARACTERISTICS:
        ( A ) LENGTH: 509 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met | Gly | Val | Leu | Lys | Phe | Lys | His | Ile | Phe | Phe | Arg | Ser | Phe | Val | Lys |
| 1 | | | | 5 | | | | | 10 | | | | | 15 | |
| Ser | Ser | Gly | Val | Ser | Gln | Ile | Val | Phe | Thr | Phe | Leu | Leu | Ile | Pro | Cys |
| | | | 20 | | | | | 25 | | | | | 30 | | |
| Cys | Leu | Thr | Leu | Asn | Phe | Arg | Ala | Pro | Pro | Val | Ile | Pro | Asn | Val | Pro |
| | | 35 | | | | | 40 | | | | | 45 | | | |
| Phe | Leu | Trp | Ala | Trp | Asn | Ala | Pro | Ser | Glu | Phe | Cys | Leu | Gly | Lys | Phe |
| | 50 | | | | | 55 | | | | | 60 | | | | |
| Asp | Glu | Pro | Leu | Asp | Met | Ser | Leu | Phe | Ser | Phe | Ile | Gly | Ser | Pro | Arg |
| 65 | | | | | 70 | | | | | 75 | | | | | 80 |
| Ile | Asn | Ala | Thr | Gly | Gln | Gly | Val | Thr | Ile | Phe | Tyr | Val | Asp | Arg | Leu |
| | | | | 85 | | | | | 90 | | | | | 95 | |
| Gly | Tyr | Tyr | Pro | Tyr | Ile | Asp | Ser | Ile | Thr | Gly | Val | Thr | Val | Asn | Gly |
| | | | 100 | | | | | 105 | | | | | 110 | | |
| Gly | Ile | Pro | Gln | Lys | Ile | Ser | Leu | Gln | Asp | His | Leu | Asp | Lys | Ala | Lys |
| | | 115 | | | | | 120 | | | | | 125 | | | |
| Lys | Asp | Ile | Thr | Phe | Tyr | Met | Pro | Val | Asp | Asn | Leu | Gly | Met | Ala | Val |
| | 130 | | | | | 135 | | | | | 140 | | | | |
| Ile | Asp | Trp | Glu | Glu | Trp | Arg | Pro | Thr | Trp | Ala | Arg | Asn | Trp | Lys | Pro |
| 145 | | | | | 150 | | | | | 155 | | | | | 160 |
| Lys | Asp | Val | Tyr | Lys | Asn | Arg | Ser | Ile | Glu | Leu | Val | Gln | Gln | Gln | Asn |
| | | | | 165 | | | | | 170 | | | | | 175 | |
| Val | Gln | Leu | Ser | Leu | Thr | Glu | Ala | Thr | Glu | Lys | Ala | Lys | Gln | Glu | Phe |

|  |  |  |  |  | 180 |  |  |  |  | 185 |  |  |  |  | 190 |  |  |
|---|---|---|---|---|---|---|---|---|---|---|---|---|---|---|---|---|---|
| Glu | Lys | Ala | Gly | Lys | Asp | Phe | Leu | Val | Glu | Thr | Ile | Lys | Leu | Gly | Lys |
|  |  | 195 |  |  |  |  | 200 |  |  |  |  | 205 |  |  |  |
| Leu | Leu | Arg | Pro | Asn | His | Leu | Trp | Gly | Tyr | Tyr | Leu | Phe | Pro | Asp | Cys |
|  |  | 210 |  |  |  |  | 215 |  |  |  |  | 220 |  |  |  |
| Tyr | Asn | His | His | Tyr | Lys | Lys | Pro | Gly | Tyr | Asn | Gly | Ser | Cys | Phe | Asn |
| 225 |  |  |  |  | 230 |  |  |  |  | 235 |  |  |  |  | 240 |
| Val | Glu | Ile | Lys | Arg | Asn | Asp | Asp | Leu | Ser | Trp | Leu | Trp | Asn | Glu | Ser |
|  |  |  |  | 245 |  |  |  |  | 250 |  |  |  |  | 255 |  |
| Thr | Ala | Leu | Tyr | Pro | Ser | Ile | Tyr | Leu | Asn | Thr | Gln | Gln | Ser | Pro | Val |
|  |  |  | 260 |  |  |  |  | 265 |  |  |  |  | 270 |  |  |
| Ala | Ala | Thr | Leu | Tyr | Val | Arg | Asn | Arg | Val | Arg | Glu | Ala | Ile | Arg | Val |
|  |  | 275 |  |  |  |  | 280 |  |  |  |  | 285 |  |  |  |
| Ser | Lys | Ile | Pro | Asp | Ala | Lys | Ser | Pro | Leu | Pro | Val | Phe | Ala | Tyr | Thr |
|  | 290 |  |  |  |  | 295 |  |  |  |  | 300 |  |  |  |  |
| Arg | Ile | Val | Phe | Thr | Asp | Gln | Val | Leu | Lys | Phe | Leu | Ser | Gln | Asp | Glu |
| 305 |  |  |  |  | 310 |  |  |  |  | 315 |  |  |  |  | 320 |
| Leu | Val | Tyr | Thr | Phe | Gly | Glu | Thr | Val | Ala | Leu | Gly | Ala | Ser | Gly | Ile |
|  |  |  |  | 325 |  |  |  |  | 330 |  |  |  |  | 335 |  |
| Val | Ile | Trp | Gly | Thr | Leu | Ser | Ile | Met | Arg | Ser | Met | Lys | Ser | Cys | Leu |
|  |  |  | 340 |  |  |  |  | 345 |  |  |  |  | 350 |  |  |
| Leu | Leu | Asp | Asn | Tyr | Met | Glu | Thr | Ile | Leu | Asn | Pro | Tyr | Ile | Ile | Asn |
|  |  | 355 |  |  |  |  | 360 |  |  |  |  | 365 |  |  |  |
| Val | Thr | Leu | Ala | Ala | Lys | Met | Cys | Ser | Gln | Val | Leu | Cys | Gln | Glu | Gln |
| 370 |  |  |  |  | 375 |  |  |  |  | 380 |  |  |  |  |  |
| Gly | Val | Cys | Ile | Arg | Lys | Asn | Trp | Asn | Ser | Ser | Asp | Tyr | Leu | His | Leu |
| 385 |  |  |  |  | 390 |  |  |  |  | 395 |  |  |  |  | 400 |
| Asn | Pro | Asp | Asn | Phe | Ala | Ile | Gln | Leu | Glu | Lys | Gly | Gly | Lys | Phe | Thr |
|  |  |  |  | 405 |  |  |  |  | 410 |  |  |  |  | 415 |  |
| Val | Arg | Gly | Lys | Pro | Thr | Leu | Glu | Asp | Leu | Glu | Gln | Phe | Ser | Glu | Lys |
|  |  |  | 420 |  |  |  |  | 425 |  |  |  |  | 430 |  |  |
| Phe | Tyr | Cys | Ser | Cys | Tyr | Ser | Thr | Leu | Ser | Cys | Lys | Glu | Lys | Ala | Asp |
|  |  | 435 |  |  |  |  | 440 |  |  |  |  | 445 |  |  |  |
| Val | Lys | Asp | Thr | Asp | Ala | Val | Asp | Val | Cys | Ile | Ala | Asp | Gly | Val | Cys |
|  | 450 |  |  |  |  | 455 |  |  |  |  | 460 |  |  |  |  |
| Ile | Asp | Ala | Phe | Leu | Lys | Pro | Pro | Met | Glu | Thr | Glu | Glu | Pro | Gln | Ile |
| 465 |  |  |  |  | 470 |  |  |  |  | 475 |  |  |  |  | 480 |
| Phe | Tyr | Asn | Ala | Ser | Pro | Ser | Thr | Leu | Ser | Ala | Thr | Met | Phe | Ile | Val |
|  |  |  |  | 485 |  |  |  |  | 490 |  |  |  |  | 495 |  |
| Ser | Ile | Leu | Phe | Leu | Ile | Ile | Ser | Ser | Val | Ala | Ser | Leu |  |  |  |
|  |  |  | 500 |  |  |  |  | 505 |  |  |  |  |  |  |  |

( 2 ) INFORMATION FOR SEQ ID NO:7:

( i ) SEQUENCE CHARACTERISTICS:
        ( A ) LENGTH: 1674 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..825

( x i ) SEQUENCE DESCRIPTION: SEQ ID NO:7:

| GGA | AGT | TGC | TTC | AAT | GTA | GAA | ATA | AAA | AGA | AAT | GAT | GAT | CTC | AGC | TGG | 48 |
|---|---|---|---|---|---|---|---|---|---|---|---|---|---|---|---|---|
| Gly | Ser | Cys | Phe | Asn | Val | Glu | Ile | Lys | Arg | Asn | Asp | Asp | Leu | Ser | Trp |  |
| 1 |  |  |  | 5 |  |  |  |  | 10 |  |  |  |  | 15 |  |  |

| | | | | | | | | | | | | | | | | |
|---|---|---|---|---|---|---|---|---|---|---|---|---|---|---|---|---|
| TTG | TGG | AAT | GAA | AGC | ACT | GCT | CTT | TAC | CCA | TCC | ATT | TAT | TTG | AAC | ACT | 96 |
| Leu | Trp | Asn | Glu | Ser | Thr | Ala | Leu | Tyr | Pro | Ser | Ile | Tyr | Leu | Asn | Thr | |
| | | | 20 | | | | | 25 | | | | | 30 | | | |
| CAG | CAG | TCT | CCT | GTA | GCT | GCT | ACA | CTC | TAT | GTG | CGC | AAT | CGA | GTT | CGG | 144 |
| Gln | Gln | Ser | Pro | Val | Ala | Ala | Thr | Leu | Tyr | Val | Arg | Asn | Arg | Val | Arg | |
| | | 35 | | | | | 40 | | | | | 45 | | | | |
| GAA | GCC | ATC | AGA | GTT | TCC | AAA | ATA | CCT | GAT | GCA | AAA | AGT | CCA | CTT | CCG | 192 |
| Glu | Ala | Ile | Arg | Val | Ser | Lys | Ile | Pro | Asp | Ala | Lys | Ser | Pro | Leu | Pro | |
| | 50 | | | | | 55 | | | | | 60 | | | | | |
| GTT | TTT | GCA | TAT | ACC | CGC | ATA | GTT | TTT | ACT | GAT | CAA | GTT | TTG | AAA | TTC | 240 |
| Val | Phe | Ala | Tyr | Thr | Arg | Ile | Val | Phe | Thr | Asp | Gln | Val | Leu | Lys | Phe | |
| 65 | | | | | 70 | | | | | 75 | | | | | 80 | |
| CTT | TCT | CAA | GAT | GAA | CTT | GTG | TAT | ACA | TTT | GGC | GAA | ACT | GTT | GCT | CTG | 288 |
| Leu | Ser | Gln | Asp | Glu | Leu | Val | Tyr | Thr | Phe | Gly | Glu | Thr | Val | Ala | Leu | |
| | | | | 85 | | | | | 90 | | | | | 95 | | |
| GGT | GCT | TCT | GGA | ATT | GTA | ATA | TGG | GGA | ACC | CTC | AGT | ATA | ATG | CGA | AGT | 336 |
| Gly | Ala | Ser | Gly | Ile | Val | Ile | Trp | Gly | Thr | Leu | Ser | Ile | Met | Arg | Ser | |
| | | | 100 | | | | | 105 | | | | | 110 | | | |
| ATG | AAA | TCT | TGC | TTG | CTC | CTA | GAC | AAT | TAC | ATG | GAG | ACT | ATA | CTG | AAT | 384 |
| Met | Lys | Ser | Cys | Leu | Leu | Leu | Asp | Asn | Tyr | Met | Glu | Thr | Ile | Leu | Asn | |
| | | 115 | | | | | 120 | | | | | 125 | | | | |
| CCT | TAC | ATA | ATC | AAC | GTC | ACA | CTA | GCA | GCC | AAA | ATG | TGT | AGC | CAA | GTG | 432 |
| Pro | Tyr | Ile | Ile | Asn | Val | Thr | Leu | Ala | Ala | Lys | Met | Cys | Ser | Gln | Val | |
| | 130 | | | | | 135 | | | | | 140 | | | | | |
| CTT | TGC | CAG | GAG | CAA | GGA | GTG | TGT | ATA | AGG | AAA | AAC | TGG | AAT | TCA | AGT | 480 |
| Leu | Cys | Gln | Glu | Gln | Gly | Val | Cys | Ile | Arg | Lys | Asn | Trp | Asn | Ser | Ser | |
| 145 | | | | | 150 | | | | | 155 | | | | | 160 | |
| GAC | TAT | CTT | CAC | CTC | AAC | CCA | GAT | AAT | TTT | GCT | ATT | CAA | CTT | GAG | AAA | 528 |
| Asp | Tyr | Leu | His | Leu | Asn | Pro | Asp | Asn | Phe | Ala | Ile | Gln | Leu | Glu | Lys | |
| | | | | 165 | | | | | 170 | | | | | 175 | | |
| GGT | GGA | AAG | TTC | ACA | GTA | CGT | GGA | AAA | CCG | ACA | CTT | GAA | GAC | CTG | GAG | 576 |
| Gly | Gly | Lys | Phe | Thr | Val | Arg | Gly | Lys | Pro | Thr | Leu | Glu | Asp | Leu | Glu | |
| | | | 180 | | | | | 185 | | | | | 190 | | | |
| CAA | TTT | TCT | GAA | AAA | TTT | TAT | TGC | AGC | TGT | TAT | AGC | ACC | TTG | AGT | TGT | 624 |
| Gln | Phe | Ser | Glu | Lys | Phe | Tyr | Cys | Ser | Cys | Tyr | Ser | Thr | Leu | Ser | Cys | |
| | | 195 | | | | | 200 | | | | | 205 | | | | |
| AAG | GAG | AAA | GCT | GAT | GTA | AAA | GAC | ACT | GAT | GCT | GTT | GAT | GTG | TGT | ATT | 672 |
| Lys | Glu | Lys | Ala | Asp | Val | Lys | Asp | Thr | Asp | Ala | Val | Asp | Val | Cys | Ile | |
| | 210 | | | | | 215 | | | | | 220 | | | | | |
| GCT | GAT | GGT | GTC | TGT | ATA | GAT | GCT | TTT | CTA | AAA | CCT | CCC | ATG | GAG | ACA | 720 |
| Ala | Asp | Gly | Val | Cys | Ile | Asp | Ala | Phe | Leu | Lys | Pro | Pro | Met | Glu | Thr | |
| 225 | | | | | 230 | | | | | 235 | | | | | 240 | |
| GAA | GAA | CCT | CAA | ATT | TTC | TAC | AAT | GCT | TCA | CCC | TCC | ACA | CTA | TCT | GCC | 768 |
| Glu | Glu | Pro | Gln | Ile | Phe | Tyr | Asn | Ala | Ser | Pro | Ser | Thr | Leu | Ser | Ala | |
| | | | | 245 | | | | | 250 | | | | | 255 | | |
| ACA | ATG | TTC | ATT | GAT | CTT | TGT | GAC | CTG | TAT | CTT | GTG | CCA | ACC | TCC | TAT | 816 |
| Thr | Met | Phe | Ile | Asp | Leu | Cys | Asp | Leu | Tyr | Leu | Val | Pro | Thr | Ser | Tyr | |
| | | | 260 | | | | | 265 | | | | | 270 | | | |
| CTC | ATC | CTG | TGACTAAGAA | TACTTAACCT | CCTGGGAGGG | CAGCTCAGGA | | | | | | | | | | 865 |
| Leu | Ile | Leu | | | | | | | | | | | | | | |
| | | 275 | | | | | | | | | | | | | | |

| | | | | | |
|---|---|---|---|---|---|
| GGTGTCAGCC | TCATTTTACC | CAGCCCTATT | CAAGATGGAG | TCACTCTGGT | TCCAATGCTT | 925 |
| CTGACAGCAG | TAGAGATAAC | ACAGTATTCA | AGCAAGAGAA | CAGAGCTCCT | GATCACCTGT | 985 |
| GTGCGTCCTT | TGAGTGGATG | GCAGCTGCAT | CTCTGCATTA | CAGCTAGTTA | GAATGATGAG | 1045 |
| TCCTTGCTAT | GCCTCAAGCA | CTGTTTCGAG | TGTTTGATGT | CTATTATCTC | ACTTCATCCT | 1105 |
| CACCAGGACC | CCATCCGAGC | CTTAATTTCA | GTTGACAGTA | ACTATTGGAT | CCCCAGGAAT | 1165 |
| ATGTTTGCAT | ATTTGGGGAG | AAAATACTAT | TGGAGGGGAA | CAGAAATGCT | ACTAAGGGTC | 1225 |

```
TCACTGTGTC ACCCAGGCTG GAGTCCATCA AAGCTCACTG CAGCCTTAAC CTTCTGTGCT    1285

CAAGGGATCC TCCCACTTAA GCCTCCTGAG TAGCTGGAAC TACAGGCATA TGCCACCGAG    1345

CCTGGCTAAT CTTTGATTTT TTTGTACAGA TTGTGTCTCC TTATGTTGCT CAGGCTGGAC    1405

TCAAACTTCT GGTCTCAAGC GATCTTTCCA TCTTAGCTTC CCAAATTGTT GGAATTATGG    1465

ACATGAGCCA GTGTGCTTGG CCTGATTTTT TTTTTTTTT TAATGAGAAA AACGTTCCTT    1525

AAGAAAAGTT TCATTGTAAG ACGAGGACTT GCTATGTTGC CAGTTTGGTC TTGAACTCGG    1585

TCTCAAGTGA TTCTCCTGCC TTGGGTTCCC AAAGCGTTTG GGCCGGCAGA TGTCAGCCAC    1645

ACCGCGCCTG CCTTATTCTT ATAAACTCA                                      1674
```

( 2 ) INFORMATION FOR SEQ ID NO:8:

( i ) SEQUENCE CHARACTERISTICS:
( A ) LENGTH: 275 amino acids
( B ) TYPE: amino acid
( D ) TOPOLOGY: linear ( i i ) MOLECULE TYPE: protein ( x i ) SEQUENCE DESCRIPTION: SEQ ID NO:8:

```
Gly Ser Cys Phe Asn Val Glu Ile Lys Arg Asn Asp Asp Leu Ser Trp
 1               5                  10                  15

Leu Trp Asn Glu Ser Thr Ala Leu Tyr Pro Ser Ile Tyr Leu Asn Thr
                20                  25                  30

Gln Gln Ser Pro Val Ala Ala Thr Leu Tyr Val Arg Asn Arg Val Arg
            35                  40                  45

Glu Ala Ile Arg Val Ser Lys Ile Pro Asp Ala Lys Ser Pro Leu Pro
     50                  55                  60

Val Phe Ala Tyr Thr Arg Ile Val Phe Thr Asp Gln Val Leu Lys Phe
65                  70                  75                  80

Leu Ser Gln Asp Glu Leu Val Tyr Thr Phe Gly Glu Thr Val Ala Leu
                85                  90                  95

Gly Ala Ser Gly Ile Val Ile Trp Gly Thr Leu Ser Ile Met Arg Ser
            100                 105                 110

Met Lys Ser Cys Leu Leu Leu Asp Asn Tyr Met Glu Thr Ile Leu Asn
        115                 120                 125

Pro Tyr Ile Ile Asn Val Thr Leu Ala Ala Lys Met Cys Ser Gln Val
    130                 135                 140

Leu Cys Gln Glu Gln Gly Val Cys Ile Arg Lys Asn Trp Asn Ser Ser
145                 150                 155                 160

Asp Tyr Leu His Leu Asn Pro Asp Asn Phe Ala Ile Gln Leu Glu Lys
                165                 170                 175

Gly Gly Lys Phe Thr Val Arg Gly Lys Pro Thr Leu Glu Asp Leu Glu
            180                 185                 190

Gln Phe Ser Glu Lys Phe Tyr Cys Ser Cys Tyr Ser Thr Leu Ser Cys
        195                 200                 205

Lys Glu Lys Ala Asp Val Lys Asp Thr Asp Ala Val Asp Val Cys Ile
    210                 215                 220

Ala Asp Gly Val Cys Ile Asp Ala Phe Leu Lys Pro Pro Met Glu Thr
225                 230                 235                 240

Glu Glu Pro Gln Ile Phe Tyr Asn Ala Ser Pro Ser Thr Leu Ser Ala
                245                 250                 255
```

```
Thr Met Phe Ile Asp Leu Cys Asp Leu Tyr Leu Val Pro Thr Ser Tyr
            260             265                 270

Leu Ile Leu
        275
```